United States Patent [19]
Tung et al.

[11] Patent Number: 5,883,252
[45] Date of Patent: Mar. 16, 1999

[54] ASPARTYL PROTEASE INHIBITORS

[75] Inventors: Roger Dennis Tung, Arlington; Francesco Gerald Salituro, Marlborough; David D. Deininger, Arlington; Govinda Rao Bhisetti, Lexington; Christopher Todd Baker, Waltham, all of Mass.

[73] Assignee: Vertex Pharmaceuticals Incorporated, Cambridge, Mass.

[21] Appl. No.: 592,777

[22] Filed: Jan. 26, 1996

[51] Int. Cl.$^6$ .................. C07D 307/20; C07D 319/06; C07D 493/04; C07D 211/60; C07D 241/04; C07D 277/06

[52] U.S. Cl. .................. 544/71; 514/193; 514/255; 514/361; 514/372; 514/397; 514/398; 514/424; 544/231; 544/336; 544/384; 548/127; 548/206; 548/311.1; 548/323.5; 548/324.1; 548/550

[58] Field of Search .................. 548/323.5, 324.1, 548/127, 206, 311.1, 397, 550; 514/398, 193, 255, 361, 372, 397, 424; 544/71, 231, 336, 384

[56] References Cited

U.S. PATENT DOCUMENTS

| | | | |
|---|---|---|---|
| 3,882,120 | 5/1975 | Piesch et al. | 548/323.5 X |
| 4,330,542 | 5/1982 | Descamps et al. | 424/248.5 |
| 4,413,130 | 11/1983 | White | 548/323.5 X |
| 4,629,724 | 12/1986 | Ryono et al. | 514/18 |
| 5,196,438 | 3/1993 | Martin et al. | 514/311 |
| 5,288,873 | 2/1994 | Su et al. | 548/323.5 |
| 5,354,866 | 10/1994 | Kempf et al. | 546/265 |
| 5,413,999 | 5/1995 | Vacca et al. | 514/231.5 |
| 5,436,351 | 7/1995 | Coffey et al. | 548/324.1 |

FOREIGN PATENT DOCUMENTS

| | | |
|---|---|---|
| 0 264 795 | 4/1988 | European Pat. Off. . |
| 0 541 168 | 5/1993 | European Pat. Off. . |
| 0 560 268 | 9/1993 | European Pat. Off. . |
| 0 560 269 | 9/1993 | European Pat. Off. . |
| 2288801 | 11/1995 | United Kingdom . |
| WO 94/19329 | 9/1994 | WIPO . |
| WO 84/26717 | 11/1994 | WIPO . |
| WO 95/24385 | 9/1995 | WIPO . |

OTHER PUBLICATIONS

Marquez et al., J. Org. Chem., vol. 37, No. 16, pp. 2558 to 2561 (1972).

J.C. Craig et al., "Antiviral Synergy Between Inhibitors of HIV Proteinase and Reverse Transcriptase", *Antiviral Chem. and Chemotherapy*, 4(3), pp. 161–166 (1990).

J.R. Huff, "HIV Protease: A Novel Chemotherapeutic Target for AIDS", *Journal of Medicinal Chemistry*, 34(8), pp. 2305–2314 (1991).

M. Miller et al., "Structure of Complex of Synthetic HIV–1 Protease with a Substrate–Based Inhibitor at 2.3 Å Resolution", *Science*, 246, pp. 1149–1152 (1989).

K.H.M. Murthy et al., "The Crystal Structures at 2.2–Å Resolution of Hydroxyethylene–Based Inhibitors Bound to Human Immunodeficiency Virus Type 1 Protease Show That the Inhibitors Are Present in Two Distinct Orientations", *J. Biol. Chem.*, 267, pp. 22770–22778 (1992).

N.A. Roberts et al., "Rational Design of Peptide–Based HIV Proteinase Inhibitors", *Science*, 248, pp. 358–361 (1990).

S. Scharpe et al., "Proteases and Their Inhibitors: Today and Tomorrow", *Biochimie*, 73, pp. 121–126 (1991).

*Primary Examiner*—Floyd D. Higel
*Attorney, Agent, or Firm*—Fish & Neave; James F. Haley, Jr.; N. Govindaswamy

[57] ABSTRACT

This invention relates to a novel class of compounds that are aspartyl protease inhibitors. In one embodiment, this invention relates to a novel class of aspartyl protease inhibitors characterized by specific structural and physicochemical features. This invention also relates to pharmaceutical compositions comprising these compounds. The compounds and pharmaceutical compositions of this invention are particularly well suited for inhibiting HIV-1 and HIV-2 protease activity and consequently, may be advantageously used as anti-viral agents against the HIV-1 and HIV-2 viruses. This invention also relates to methods for inhibiting aspartyl protease activity and methods for treating viral infections using the compounds and compositions of this invention.

26 Claims, No Drawings

ASPARTYL PROTEASE INHIBITORS

TECHNICAL FIELD OF THE INVENTION

The present invention relates to a novel class of compounds which are aspartyl protease inhibitors. In one embodiment, this invention relates to a novel class of HIV aspartyl protease inhibitors characterized by specific structural and physicochemical features. This invention also relates to pharmaceutical compositions comprising these compounds. The compounds and pharmaceutical compositions of this invention are particularly well suited for inhibiting HIV-1 and HIV-2 protease activity and consequently, may be advantageously used as anti-viral agents against the HIV-1 and HIV-2 viruses. This invention also relates to methods for inhibiting aspartyl protease activity and methods for treating viral infections using the compounds and compositions of this invention.

BACKGROUND OF THE INVENTION

The human immunodeficiency virus ("HIV") is the causative agent for acquired immunodeficiency syndrome ("AIDS")—a disease characterized by the destruction of the immune system, particularly of $CD4^+$ T-cells, with attendant susceptibility to opportunistic infections—and its precursor AIDS-related complex ("ARC")—a syndrome characterized by symptoms such as persistent generalized lymphadenopathy, fever and weight loss.

As in the case of several other retroviruses, HIV encodes the production of a protease which carries out post-translational cleavage of precursor polypeptides in a process necessary for the formation of infectious virions (S. Crawford et al., "A Deletion Mutation in the 5' Part of the pol Gene of Moloney Murine Leukemia Virus Blocks Proteolytic Processing of the gag and pol Polyproteins", *J. Virol.*, 53, p. 899 (1985)). These gene products include pol, which encodes the virion RNA-dependent DNA polymerase (reverse transcriptase), an endonuclease, HIV protease, and Gag, which encodes the core-proteins of the virion (H. Toh et al., "Close Structural Resemblance Between Putative Polymerase of a Drosophila Transposable Genetic Element 17.6 and pol gene product of Moloney Murine Leukemia Virus", *EMBO J.*, 4, p. 1267 (1985); L. H. Pearl et al., "A Structural Model for the Retroviral Proteases", *Nature*, pp. 329–351 (1987); M. D. Power et al., "Nucleotide Sequence of SRV-1, a Type D Simian Acquired Immune Deficiency Syndrome Retrovirus", *Science*, 231, p. 1567 (1986)).

A number of synthetic anti-viral agents have been designed to target various stages in the replication cycle of HIV. These agents include compounds which block viral binding to $CD4^+$ T-lymphocytes (for example, soluble CD4), and compounds which interfere with viral replication by inhibiting viral reverse transcriptase (for example, didanosine and zidovudine (AZT)) and inhibit integration of viral DNA into cellular DNA (M. S. Hirsh and R. T. D'Aqulia, "Therapy for Human Immunodeficiency Virus Infection", *N.Eng.J.Med.*, 328, p. 1686 (1993)). However, such agents, which are directed primarily to early stages of viral replication, do not prevent the production of infectious virions in chronically infected cells. Furthermore, administration of some of these agents in effective amounts has led to cell-toxicity and unwanted side effects, such as anemia and bone marrow suppression.

More recently, drug design efforts have been directed toward creating compounds which inhibit the formation of infectious virions by interfering with the processing of viral polyprotein precursors. Processing of these precursor proteins requires the action of virus-encoded proteases which are essential for replication (Kohl, N. E. et al. "Active HIV Protease is Required for Viral Infectivity" *Proc. Natl. Acad. Sci. USA*, 85, p. 4686 (1988)). The anti-viral potential of HIV protease inhibition has been demonstrated using peptidal inhibitors. Such peptidal compounds, however, are typically large and complex molecules that tend to exhibit poor bioavailability and are not generally consistent with oral administration. Accordingly, the need still exists for compounds that can effectively inhibit the action of viral proteases, for use as agents for preventing and treating chronic and acute viral infections. Such agents would be expected to act as effective therapeutic agents in their own right. In addition, since they act at a separate stage in the virus life cycle from previously described antiretroviral agents, the administration of a combination of agents would be expected to result in increased therapeutic efficacy.

SUMMARY OF THE INVENTION

The present invention provides a novel class of compounds, and pharmaceutically acceptable derivatives thereof, that are useful as inhibitors of aspartyl proteases, and in particular, HIV aspartyl protease. The compounds of this invention can be used alone or in combination with other therapeutic or prophylactic agents, such as anti-virals, antibiotics, immunomodulators or vaccines, for the treatment or prophylaxis of viral infection.

According to a preferred embodiment, the compounds of this invention are capable of inhibiting HIV viral replication in human $CD_4^+$ cells including T-cells, monocytic lines including macrophages and dendrocytes and other permissive cells. These compounds are useful as therapeutic and prophylactic agents to treat or prevent infection by HIV-1 and related viruses which may result in asymptomatic infection, AIDS-related complex ("ARC"), acquired immunodeficiency syndrome ("AIDS"), or similar disease of the immune system.

It is a principal object of this invention to provide a novel class of compounds that are aspartyl protease inhibitors, and particularly, HIV aspartyl protease inhibitors. This novel class of compounds is represented by formula I:

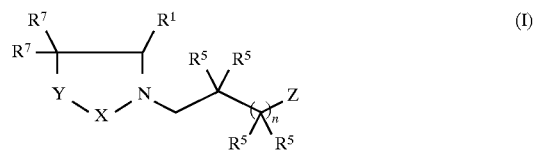

wherein
each Z is

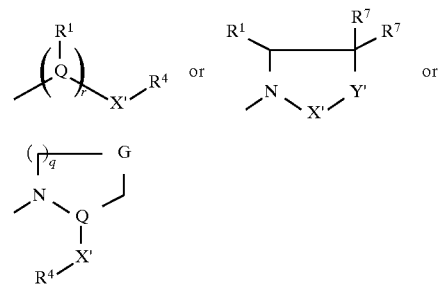

wherein any Z may be optionally fused with $R^6$;
each X and X' is independently selected from the group consisting of —C(O)—, —C(O)C(O)—, —S(O)— and —S(O)$_2$;

each Y and Y' is independently selected from the group consisting of —$(C(R^2)_2)_p$—, —$NR^2$—, —$(C(R^2)_2)_p$—M—, and —$N(R^2)$—$CH_2$—;

each $R^1$ is independently selected from the group consisting of hydrogen; $R^6$; $C_1$–$C_6$ alkyl; $C_2$–$C_6$ alkenyl; $C_2$–$C_6$ alkynyl; $C_3$–$C_6$ cycloalkyl optionally fused with $R^6$; $C_5$–$C_6$ cycloalkenyl optionally fused with $R^6$; and where $R^1$'s are attached to adjacent atoms, the $R^1$'s together with their attached adjacent atoms form a carbocyclic or heterocyclic ring system which may be optionally fused with $R^6$; where any member of $R^1$ may be optionally substituted by one or more $R^2$;

each $R^2$ is independently selected from hydrogen; $R^3$; $C_1$–$C_6$ alkyl; $C_2$–$C_6$ alkenyl; $C_2$–$C_6$ alkynyl; $C_3$–$C_6$ cycloalkyl optionally fused with $R^6$; $C_5$–$C_6$ cycloalkenyl optionally fused with $R^6$; and where two $R^2$'s are attached to the same geminal atom, the $R^2$'s together with their attached geminal atom form a spirocarbocyclic or spiroheterocyclic ring system, where any member of $R^2$ may be optionally substituted by one or more $R^3$;

each $R^3$ is independently selected from oxo, $OR^9$, $N(R^9)_2$, $N(R^9)$—X—$R^9$, $N(R^9)$—X—$OR^9$, $SR^9$, X—$R^9$, O—X—$N(R^9)_2$, $C(O)N(R^9)_2$, halogen, $NO_2$, CN, $COOR^9$ and $R^6$;

each $R^4$ is independently selected from from the group consisting of $OR^9$; $N(R^9)_2$; X—$R^9$; $C(O)N(R^9)_2$; $R^6$; $C_1$–$C_6$ alkyl; $C_2$–$C_4$ alkenyl; $C_3$–$C_6$ cycloalkyl optionally fused with $R^6$; $C_5$–$C_6$ cycloalkenyl optionally fused with $R^6$; where any member of $R^4$ may be optionally substituted by one or more groups independently selected from the group consisting of $R^9$ and $R^3$;

each $R^5$ is independently selected from the group consisting of H, OH, O and $R^1$;

each $R^6$ is independently selected from the group consisting of aryl, carbocyclyl and heterocyclyl, wherein said aryl, carbocyclyl or heterocyclyl may be optionally substituted with one or more groups selected from the group consisting of oxo, —$OR^9$, —$R^9$, —$N(R^9)$ ($R^9$), —$N(R^9)$—X—$R^9$, $SR^9$, —X—$R^9$, —O—X—$N(R^9)_2$, —$R^9$—$OR^9$, —CN, —$CO_2R^9$, —X—$N(R^9)$ ($R^9$), halogen, —$NO_2$, and —$CF_3$;

each $R^7$ is independently selected from the group consisting of hydrogen, OH and O;

each $R^8$ is independently selected from the group consisting of hydrogen, alkyl, alkenyl, alkynyl, aryl, carbocyclyl, and heterocyclyl;

each $R^9$ is independently selected from the group consisting of hydrogen, alkyl, alkenyl, alkynyl, aryl, carbocyclyl, heterocyclyl, aralkyl, carbocyclylalkyl and heterocyclylalkyl wherein any aryl, carbocyclyl or heterocyclyl may be optionally fused with $R^8$ and wherein any member of $R^8$ may be optionally substituted by one or more groups independently selected from the group consisting of —$OR^8$, —$N(R^8)_2$, —CN, —$NO_2$, —X—$R^8$, —X— $N(R^8)_2$, —$C(O)OR^8$, —$N(R^8)$—$XNR^8$, and halogen;

each Q is independently selected from CH and N;

each M is independently selected from the group consisting of NH, —$NR^2$—, —O—, —S—, —S(O)— and —$S(O)_2$—;

each n is 1 or 2;

each r is 0, 1 or 2;

each p is independently 1 or 2;

each q is independently 1, 2 or 3; and each G is independently selected from the group consisting of —NH—, —$NR^2$—, —O—, —S—, —S(O)—, $S(O)_2$, —C(O)—, and —$C(R^2)_2$—.}

It is also an object of this invention to provide pharmaceutical compositions comprising the compounds of formula I and methods for their use as inhibitors of aspartyl protease, and particularly, HIV aspartyl protease.

It is a further object of this invention to provide methods for treating viral diseases, and in particular HIV-related diseases, using the compounds and compositions of this invention.

DETAILED DESCRIPTION OF THE INVENTION

In order that the invention herein described may be more fully understood, the following detailed description is set forth. In the description, the following abbreviations are used:

| Designation | Reagent or Fragment |
| --- | --- |
| Ac | acetyl |
| Me | methyl |
| Et | ethyl |
| Bn | benzyl |
| Trityl | triphenylmethyl |
| Asn | D- or L-asparagine |
| Ile | D- or L-isoleucine |
| Phe | D- or L-phenylalanine |
| Val | D- or L-valine |
| Boc | tert-butoxycarbonyl |
| Cbz | benzyloxycarbonyl (carbobenzyloxy) |
| Fmoc | 9-fluorenylmethoxycarbonyl |
| DCC | dicyclohexylcarbodiimide |
| DIC | diisopropylcarbodiimide |
| EDC | 1-(3-dimethylaminopropyl)-3-ethylcarbodiimide hydrochloride |
| HOBt | 1-hydroxybenzotriazole |
| HOSu | 1-hydroxysuccinimide |
| TFA | trifluoroacetic acid |
| DIEA | diisopropylethylamine |
| DBU | 1,8-diazabicyclo(5.4.0)undec-7-ene |
| EtOAc | ethyl acetate |
| t-Bu | tert-butyl |
| iBu | iso-butyl |
| DMF | dimethylformamide |
| THP | tertrahydropyran |
| THF | tetrahydrofuran |
| DMSO | dimethylsulfoxide |

The following terms are employed herein:

Unless expressly stated to the contrary, the terms "—$SO_2$—" and "—$S(O)_2$—" as used herein refer to a sulfone or sulfone derivative (i.e., both appended groups linked to the S), and not a sulfinate ester.

The term "alkoxy" refers to an alkyl ether radical, wherein the term "alkyl" is as defined above. Examples of suitable alkyl ether radicals include, but are not limited to, methoxy, ethoxy, n-propoxy, isopropoxy, n-butoxy, isobutoxy, sec-butoxy, tert-butoxy and the like.

The term "alkyl", alone or in combination with any other term, refers to a straight-chain or branch-chain saturated aliphatic hydrocarbon radical containing the specified number of carbon atoms, or where no number is specified, preferably from 1–10 and more preferably from 1–5 carbon atoms. Examples of alkyl radicals include, but are not limited to, methyl, ethyl, n-propyl, isopropyl, n-butyl, isobutyl, sec-butyl, tert-butyl, pentyl, isoamyl, n-hexyl and the like.

The term "alkenyl", alone or in combination with any other term, refers to a straight-chain or branched-chain mono- or poly-unsaturated aliphatic hydrocarbon radical containing the specified number of carbon atoms, or where no number is specified, preferably from 2–10 carbon atoms and more preferably, from 2–6 carbon atoms. Examples of alkenyl radicals include, but are not limited to, ethenyl, E- and Z-propenyl, isopropenyl, E- and Z-butenyl, E- and Z-isobutenyl, E- and Z-pentenyl, E- and Z-hexenyl, E,E-, E,Z-, Z,E- and Z,Z-hexadienyl and the like.

The term "anti-viral agent" or "anti-retroviral agent" refers to a compound or drug which possesses viral inhibitory activity. Such agents include reverse transcriptase inhibitors (including nucleoside and non-nucleoside analogs) and protease inhibitors. Preferably the protease inhibitor is an HIV protease inhibitor. Examples of nucleoside analog reverse transcriptase inhibitors include, but are not limited to, zidovudine (AZT), dideoxycytidine (ddC), didanosine (ddI), stavudine (d4T), 3TC, 935U83, 1592U89 and 524W91. Examples of non-nucleoside analog reverse transcriptase inhibitor include, but are not limited to TIBO, delavirdine (U90) and nevirapine. Examples of HIV protease inhibitors include, but are not limited to, saquinavir (Ro 31-8959, Roche), indinavir (L-735,524, Merck)), ritonavir (ABT 538, Abbott), nelfinavir (AG 1343, Agouron), palinavir (Bila 2011 BS), U-103017 (Upjohn), XM 412 (DuPont Merck), XM 450 (DuPont Merck), BMS 186318 (Bristol-Meyers Squibb) and CPG 53,437 (Ciba Geigy)

The term "aryl", alone or in combination with any other term, refers to a carbocyclic aromatic radical (such as phenyl or naphthyl) containing the specified number of carbon atoms, preferably from 6–14 carbon atoms, and more preferably from 6–10 carbon atoms. Examples of aryl radicals include, but are not limited to phenyl, naphthyl, indenyl, indanyl, azulenyl, fluorenyl, anthracenyl and the like.

The term "carbocycle" and "carbocyclyl" radical, refers to a non-aromatic stable 3- to 8-membered carbon ring which may be saturated, mono-unsaturated or poly-unsaturated. The carbocycle may be attached at any endocyclic carbon atom which results in a stable structure. Preferred carbocycles have 5–6 carbons.

The term "heterocycle" and "heterocyclyl" radical, unless otherwise defined herein, refers to a stable 3–7 membered monocyclic heterocyclic ring or 8–11 membered bicyclic heterocyclic ring which is either saturated or unsaturated, and which may be optionally benzofused if monocyclic. Each heterocycle consists of one or more carbon atoms and from one to four heteroatoms selected from the group consisting of nitrogen, oxygen and sulfur. As used herein, the terms "nitrogen and sulfur heteroatoms" include any oxidized form of nitrogen and sulfur, and the quaternized form of any basic nitrogen. In addition, any ring nitrogen may be optionally substituted with a substituent $R^2$, as defined herein for compounds of formula I. A heterocyclyl radical may be attached at any endocyclic carbon or heteroatom which results in the creation of a stable structure. Preferred heterocycles include 5–7 membered monocyclic heterocycles and 8–10 memebered bicyclic heterocycles. Preferred heterocycles defined above include, for example, benzimidazolyl, imidazolyl, imidazolinoyl, imidazolidinyl, quinolyl, isoquinolyl, indolyl, indazolyl, indazolinolyl, perhydropyridazyl, pyridazyl, pyridyl, pyrrolyl, pyrrolinyl, pyrrolidinyl, pyrazolyl, pyrazinyl, quinoxolyl, piperidinyl, pyranyl, pyrazolinyl, piperazinyl, pyrimidinyl, pyridazinyl, morpholinyl, thiamorpholinyl, furyl, thienyl, triazolyl, thiazolyl, β-carbolinyl, tetrazolyl, thiazolidinyl, benzofuranoyl, thiamorpholinyl sulfone, oxazolyl, benzoxazolyl, oxopiperidinyl, oxopyrroldinyl, oxoazepinyl, azepinyl, isoxazolyl, isothiazolyl, furazanyl, tetrahydropyranyl, tetrahydrofuranyl, thiazolyl, thiadiazoyl, dioxolyl, dioxinyl, oxathiolyl, benzodioxolyl, dithiolyl, thiophenyl, tetrahydrothiophenyl and sulfolanyl, dioxanyl, dioxolanyl, tetrahydrofurodihydrofuranyl, tetrahydropyranodihydrofuranyl, dihydropyranyl, tetrahydrofurofuranyl and tetrahydropyranofuranyl.

The term "halogen" refers to a radical of fluorine, chlorine, bromine or iodine.

The terms "HIV protease" and "HIV aspartyl protease" are used interchangeably and refer to the aspartyl protease encoded by the human immunodeficiency virus type 1 or 2. In a preferred embodiment of this invention, these terms refer to the human immunodeficiency virus type 1 aspartyl protease.

The term "substituted", whether preceded by the term "optionally" or not, and substitutions contained in formulas of this invention, refer to the replacement of one or more hydrogen radicals in a given structure with the radical of a specified substituent. When more than one position in a given structure may be substituted with more than one substituent selected from a specified group, the substituents may be either the same or different at every position (for example, the moiety $—N(R^2)(R^2)$). Typically, when a structure may be optionally substituted, 0–3 substitutions are preferred, and 0–1 substitutions is more preferred. Most preferred substituents are those which enhance protease inhibitory activity or intracellular antiviral activity in permissive mammalian cells or immortalized mammalian cell lines, or which enhance deliverability by enhancing solubility characteristics or enhancing pharmacokinetic or pharmacodynamic profiles as compared to the unsubstituted compound. Other more preferred substituents include those used in the compounds shown in Tables 1–5.

The term "pharmaceutically effective amount" refers to an amount effective in treating HIV infection in a patient either as monotherapy or in combination with other agents. The term "treating" as used herein refers to the alleviation of symptoms of a particular disorder in a patient or the improvement of an ascertainable measurement associated with a particular disorder. Specifically, with respect to HIV, effective treatment using the compounds and compositions of this invention would result in an improvement in an HIV associated ascertainable measurement. The term "prophylactically effective amount" refers to an amount effective in preventing HIV infection in a patient. As used herein, the term "patient" refers to a mammal, including a human.

The term "pharmaceutically acceptable carrier or adjuvant" refers to a carrier or adjuvant that may be administered to a patient, together with a compound of this invention, and which does not destroy the pharmacological activity thereof and is nontoxic when administered in doses sufficient to deliver a therapeutic amount of the antiretroviral agent.

As used herein, the compounds of this invention, including the compounds of formula I are defined to include pharmaceutically acceptable derivatives or prodrugs thereof. A "pharmaceutically acceptable derivative or prodrug" means any pharmaceutically acceptable salt, ester, salt of an ester, or other derivative of a compound of this invention which, upon administration to a recipient, is capable of providing (directly or indirectly) a compound of this invention or an inhibitorily active metabolite or residue thereof. Particularly favored derivatives and prodrugs are those that increase the bioavailability of the compounds of this invention when such compounds are administered to a mammal (e.g., by allowing an orally administered compound to be more readily absorbed into the blood) or which enhance delivery of the parent compound to a biological compartment (e.g., the brain or lymphatic system) relative to the parent species.

Pharmaceutically acceptable salts of the compounds of this invention include those derived from pharmaceutically acceptable inorganic and organic acids and bases. Examples of suitable acids include hydrochloric, hydrobromic, sulfuric, nitric, perchloric, fumaric, maleic, phosphoric, glycollic, lactic, salicylic, succinic, toluene-p-sulfonic, tartaric, acetic, citric, methanesulfonic, ethanesulfonic, formic, benzoic, malonic, naphthalene-2-sulfonic and benzenesulfonic acids. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium), alkaline earth metal (e.g., magnesium), ammonium and $N-(C_{1-4}\ alkyl)_4^+$ salts.

The term "thiocarbamates" refers to compounds containing the functional group $N-SO_2-O$.

The compounds of this invention contain one or more asymmetric carbon atoms and thus occur as racemates and racemic mixtures, single enantiomers, diastereomeric mixtures and individual diastereomers. All such isomeric forms of these compounds are expressly included in the present invention. Each stereogenic carbon may be of the R or S configuration. Although the specific compounds exemplified in this application may be depicted in a particular stereochemical configuration, compounds having either the opposite stereochemistry at any given chiral center or mixtures thereof are also envisioned.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a mammal or for use in affinity chromatography applications). Typically, such compounds are stable at a temperature of 40° C. or less, in the absence of moisture or other chemically reactive conditions, for at least a week.

The compounds of the present invention may be used in the form of salts derived from inorganic or organic acids. Included among such acid salts, for example, are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate and undecanoate.

This invention also envisions the quaternization of any basic nitrogen-containing groups of the compounds disclosed herein. The basic nitrogen can be quaternized with any agents known to those of ordinary skill in the art including, for example, lower alkyl halides, such as methyl, ethyl, propyl and butyl chloride, bromides and iodides; dialkyl sulfates including dimethyl, diethyl, dibutyl and diamyl sulfates; long chain halides such as decyl, lauryl, myristyl and stearyl chlorides, bromides and iodides; and aralkyl halides including benzyl and phenethyl bromides. Water or oil-soluble or dispersible products may be obtained by such quaternization.

The compounds of this invention are those of formula I:

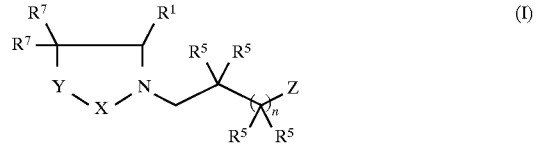

wherein
each Z is

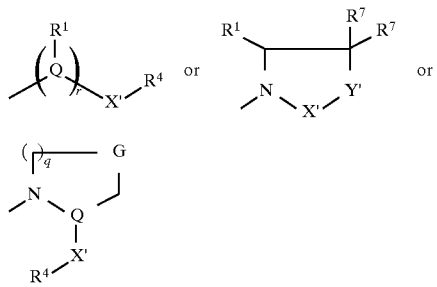

wherein any Z may be optionally fused with $R^6$;
each X and X' is independently selected from the group consisting of $-C(O)-$, $-C(O)C(O)-$, $-S(O)-$ and $-S(O)_2$;
each Y and Y' is independently selected from the group consisting of $-(C(R^2)_2)_p-$, $-NR^2-$, $-(C(R^2)_2)_p-M-$, and $-N(R^2)-CH_2-$;
each $R^1$ is independently selected from the group consisting of hydrogen; $R^6$; $C_1-C_6$ alkyl; $C_2-C_6$ alkenyl; $C_2-C_6$ alkynyl; $C_3-C_6$ cycloalkyl optionally fused with $R^6$; $C_5-C_6$ cycloalkenyl optionally fused with $R^6$; and where $R^1$'s are attached to adjacent atoms, the $R^1$'s together with their attached adjacent atoms form a carbocyclic or heterocyclic ring system which may be optionally fused with $R^6$; where any member of $R^1$ may be optionally substituted by one or more $R^2$;
each $R^2$ is independently selected from hydrogen; $R^3$; $C_1-C_6$ alkyl; $C_2-C_6$ alkenyl; $C_2-C_6$ alkynyl; $C_3-C_6$ cycloalkyl optionally fused with $R^6$; $C_5-C_6$ cycloalkenyl optionally fused with $R^6$; and where two $R^2$'s are attached to the same geminal atom, the $R^2$'s together with their attached geminal atom form a spirocarbocyclic or spiroheterocyclic ring system, where any member of $R^2$ may be optionally substituted by one or more $R^3$;
each $R^3$ is independently selected from oxo, $OR^9$, $N(R^9)_2$, $N(R^9)-X-R^9$, $N(R^9)-X-OR^9$, $SR^9$, $X-R^9$, $O-X-N(R^9)_2$, $C(O)N(R^9)_2$, halogen, $NO_2$, CN, $COOR^9$ and $R^6$;
each $R^4$ is independently selected from from the group consisting of $OR^9$; $N(R^9)_2$; $X-R^9$; $C(O)N(R^9)_2$; $R^6$; $C_1-C_6$ alkyl; $C_2-C_4$ alkenyl; $C_3-C_6$ cycloalkyl optionally fused with $R^6$; $C_5-C_6$ cycloalkenyl optionally fused with $R^6$; where any member of $R^4$ may be optionally substituted by one or more groups independently selected from the group consisting of $R^9$ and $R^3$;
each $R^5$ is independently selected from the group consisting of H, OH, O and $R^1$;

each $R^6$ is independently selected from the group consisting of aryl, carbocyclyl and heterocyclyl, wherein said aryl, carbocyclyl or heterocyclyl may be optionally substituted with one or more groups selected from the group consisting of oxo, —$OR^9$, —$R^9$, —$N(R^9)(R^9)$, —$N(R^9)$—X—$R^9$, $SR^9$, —X—$R^9$, —O—X—$N(R^9)_2$, —$R^9$—$OR^9$, —CN, —$CO_2R^9$, —X—$N(R^9)(R^9)$, halogen, —$NO_2$, and —$CF_3$;

each $R^7$ is independently selected from the group consisting of hydrogen, OH and O;

each $R^8$ is independently selected from the group consisting of hydrogen, alkyl, alkenyl, alkynyl, aryl, carbocyclyl, and heterocyclyl;

each $R^9$ is independently selected from the group consisting of hydrogen, alkyl, alkenyl, alkynyl, aryl, carbocyclyl, heterocyclyl, aralkyl, carbocyclylalkyl and heterocyclylalkyl wherein any aryl, carbocyclyl or heterocyclyl may be optionally fused with $R^8$ and wherein any member of $R^8$ may be optionally substituted by one or more groups independently selected from the group consisting of —$OR^8$, —$N(R^8)_2$, —CN, —$NO_2$, —X—$R^8$, —X—$N(R^8)_2$, —C(O)$OR^8$, —$N(R^8)$—$XNR^8$, and halogen;

each Q is independently selected from CH and N;

each M is independently selected from the group consisting of NH, —$NR^2$—, —O—, —S—, —S(O)— and —$S(O)_2$—;

each n is 1 or 2;

each r is 0, 1 or 2;

each p is independently 1 or 2;

each q is independently 1, 2 or 3; and each G is independently selected from the group consisting of —NH—, —$NR^2$—, —O—, —S—, —S(O)—, $S(O)_2$, —C(O)—, and —$C(R^2)_2$—.}

Except where expressly noted to the contrary, the term "[variable] as defined for formula I" refers to the definitions shown directly above. In addition, where no reference is made to a particular definition for a given variable, the definition is to be taken as that defined for formula I shown directly above.

Preferred compounds of formula I are those wherein n is equal to 1; those having the structure of formula II:

(II)

and those having the structure of formula III:

(III)

Also preferred are compounds according to formula I wherein X is —C(O)— or —$S(O)_2$—and Y is —$(C(R^2)_2)_p$—M—; those wherein X is —C(O)— or —$S(O)_2$— and Y is (—$C(R^2)_2$—$)_p$; those wherein X is —C(O)—, —C(O)C(O)— or —$S(O)_2$—; and Y is —$N(R^2)$— or —$N(R^2)$—$CH_2$—; those having the structure of formula IV:

(IV)

wherein

X and X' are independently —C(O)— or —$S(O)_2$—; and

Y is —$(C(R^2)_2)$—M—, —$(C(R^2)_2)_p$—, —$N(R^2)$— or —$N(R^2)$—$CH_2$—.

Also preferred are those compounds of formula I having the structure of formula V:

(V)

wherein

X is —C(O)— or —$S(O)_2$—;

Y is —$(C(R^2)_2)$—M—, —$(C(R^2)_2)_p$—, —$N(R^2)$— or —$N(R^2)$—$CH_2$—;

$R^{10}$ is O or $H_2$;

each $R^{11}$ is independently H, OH or O, where both $R^{11}$ may not simultaneously be hydrogen; and Z is a structure of formula VI:

(VI)

wherein any structure of formula VI may be optionally fused with an aryl, carbocyclic or heterocyclic ring and may be optionally substituted with 1–3 substituents independently selected from $R^2$; and compounds of formula V wherein X and X' is —C(O)—;

Y is —$(C(R^2)_2)$—;

$R^7$ is H;

$R^{10}$ is $H_2$; and one $R^{11}$ is H and one $R^{11}$ is OH; and those compounds of formula V wherein X and X' is —C(O)—;

Y is —$N(R^2)$—;

$R^7$ is H;

$R^{10}$ is $H_2$; and one $R^{11}$ is H and one $R^{11}$ is OH.

Also preferred is the compound of formula I having the structure of formula IX:

(IX)

wherein

X is —C(O)— or —$S(O)_2$—; and the compounds of formula IX wherein

X is —C(O)—;

Y is —$(C(R^2)_2)$—M—; and

R[7] is H; and those compounds of formula IX wherein
X is —C(O)—;
Y is —N(R[2])—; and
R[7] is H; and
those compounds of formula IX wherein X is —C(O)—; Y is —(C(R[2])$_2$)—; and R[7] is H.

Also preferred are those compounds of formula I having the structure of formula XII:

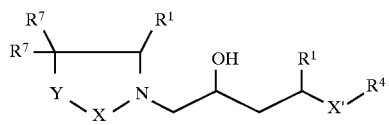
(XII)

wherein

X and X' are independently —C(O)— or —S(O)$_2$—.

Also preferred are the compounds according to formula I, having the structure of formula XIII:

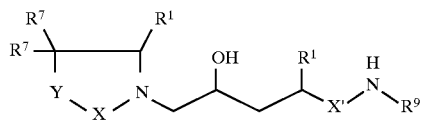
(XIII)

wherein

X and X' are independently —C(O)— or —S(O)$_2$—.

In an alternate embodiment, preferred compounds are those of formula V wherein
R[10] is H$_2$; and
one R[11] is H and one R[11] is OH; and
Z is selected from the group consisting of:

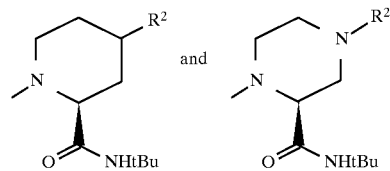

and R[2] is as defined in claim 1; and those of formula V wherein Z is selected from the group consisting of

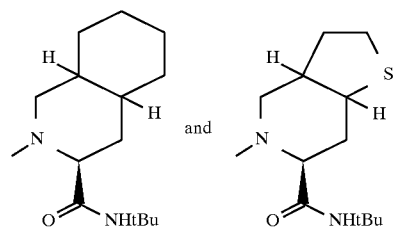

R[10] is H$_2$; and
one R[11] is H and one R[11] is OH.

Also preferred are those compounds of formula V wherein
X and X' is —C(O)—;
Y is —(C(R[2])$_2$)—;
R[7] is H;
R[10] is H$_2$; and
one R[11] is H and one R[11] is OH; and those compounds of formula V wherein
X and X' is —C(O)—;
Y is —N(R[2])—;
R[7] is H;
R[10] is H$_2$; and
one R[11] is H and one R[11] is OH, and wherein Z is selected from the group consisting of:

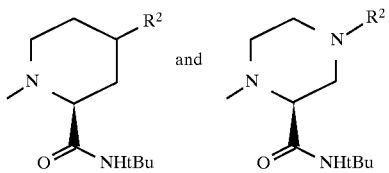

and R[2] is as defined in claim 1.

Also preferred are those compounds of formula V wherein
X and X' is —C(O)—;
Y is —(C(R[2])$_2$)—;
R[7] is H;
R[10] is H$_2$; and
one R[11] is H and one R[11] is OH; and those compounds of formula V wherein
X and X' is —C(O)—;
Y is —N(R[2])—;
R[7] is H;
R[10] is H$_2$; and
one R[11] is H and one R[11] is OH, and wherein Z is selected from the group consisting of:

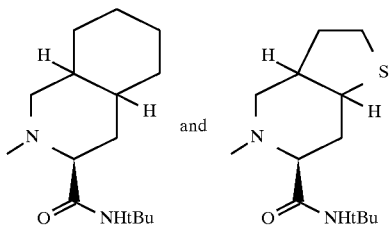

Also preferred are compounds of formula I wherein
Z is selected from the group consisting of —XR[4], —N(R[1])—X—R[4], —N(R[1])—N(R[1])—X—R[4], and formula VI; wherein any structure of formula VI may be optionally fused with an aryl, carbocyclic or heterocyclic ring and may be optionally substituted with 1–3 members independently selected from R[2].

In another embodiment, compounds of formula I with structures VII, VIII, IX, and X are preferred:

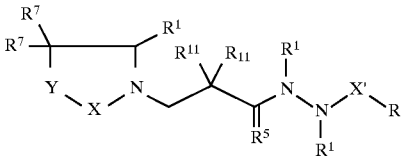
(VII)

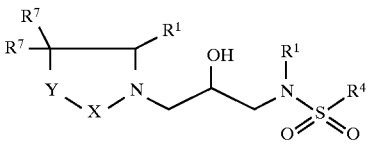
(IX)

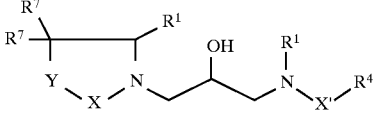
(VIII)

-continued

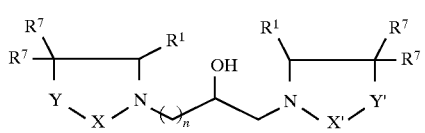

(X)

where all definitions of variables for formula I apply.

Preferred R² groups for formula I include: $C_1$–$C_6$ alkyl and alkenyl optionally substituted with $R^6$; where two $R^2$ taken together form a spriocyclic ring and $C_3$–$C_6$ cycloalkyl or cycloalkenyl optionally fused with $R^6$.

Preferred compounds of this invention of formula I include the specific compounds contained in Tables 1–5.

TABLE 1

| Cmpd. No. | A | Z |
|---|---|---|
| 1 | | |
| 2 | | |
| 3 | | |
| 4 | | |
| 5 | | |
| 6 | | |

TABLE 1-continued
A—CH2—CH(OH)—CH2—Z
| Cmpd. No. | A | Z |
|---|---|---|
| 7 | 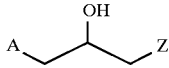 | 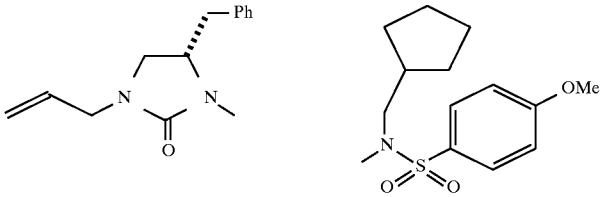 |
| 8 | 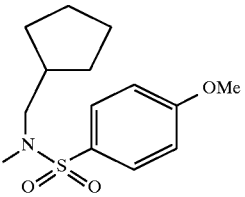 | 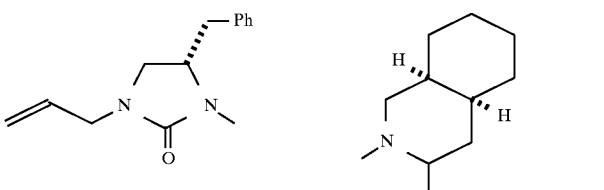 |
| 9 | 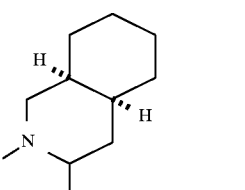 | 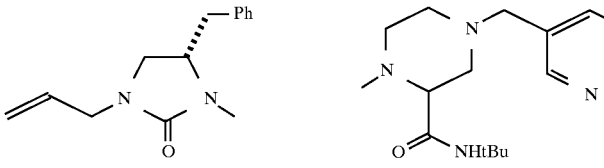 |
| 10 | 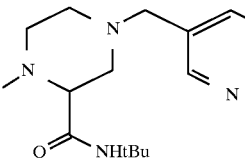 | 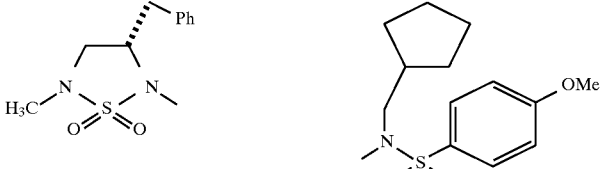 |
| 11 | 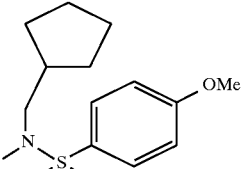 |  |
| 12 | 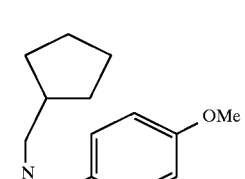 | 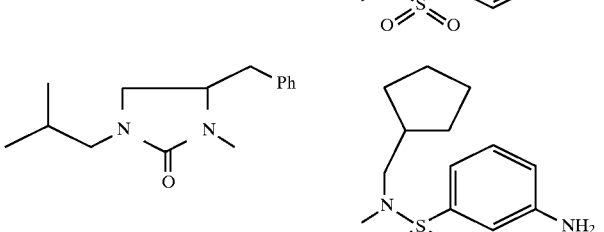 |
| 13 | 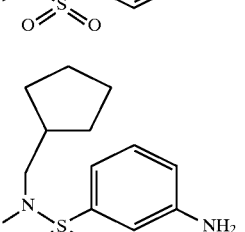 | 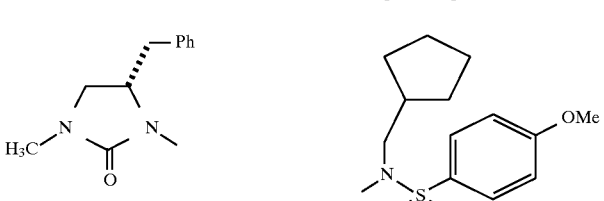 |

TABLE 1-continued $$A\diagdown\underset{OH}{\diagup}\diagdown Z$$

| Cmpd. No. | A | Z |
|---|---|---|
| 14 | (1-benzyl-3-methyl-4(S)-benzyl-imidazolidin-2-one) | CH₂-cyclopentyl, N(Me)SO₂-C₆H₄-4-OMe |
| 15 | (1-methyl-5(S)-benzyl-pyrrolidin-2-one) | CH₂-cyclopentyl, N(Me)SO₂-C₆H₄-4-OMe |
| 16 | (1-methyl-3-methyl-5(S)-benzyl-pyrrolidin-2-one) | CH₂-cyclopentyl, N(Me)SO₂-C₆H₄-4-OMe |
| 17 | (1-methyl-3,3-dimethyl-5(S)-benzyl-pyrrolidin-2-one) | CH₂-cyclopentyl, N(Me)SO₂-C₆H₄-4-OMe |
| 18 | (1-methyl-3-ethyl-5(S)-benzyl-pyrrolidin-2-one) | CH₂-cyclopentyl, N(Me)SO₂-C₆H₄-4-OMe |
| 19 | (1-methyl-3-hydroxy-5(S)-benzyl-pyrrolidin-2-one) | CH₂-cyclopentyl, N(Me)SO₂-C₆H₄-4-OMe |
| 20 | (1-methyl-3-benzyl-5(S)-benzyl-pyrrolidin-2-one) | CH₂-cyclopentyl, N(Me)SO₂-C₆H₄-4-OMe |

TABLE 1-continued $$A\diagdown\underset{\text{OH}}{\diagup}Z$$

| Cmpd. No. | A | Z |
|---|---|---|
| 21 | (2-amino-4-phenyl group with N-methyl amide) | cyclopentylmethyl-N-methyl-4-methoxybenzenesulfonamide |
| 22 | (2-acetamido-4-phenyl group with N-methyl amide) | cyclopentylmethyl-N-methyl-4-methoxybenzenesulfonamide |
| 23 | (dihydroxy-phenyl group with N-methyl amide) | cyclopentylmethyl-N-methyl-4-methoxybenzenesulfonamide |
| 24 | (methylenedioxy-phenyl group with N-methyl amide) | cyclopentylmethyl-N-methyl-4-methoxybenzenesulfonamide |
| 25 | (diacetoxy-phenyl group with N-methyl amide) | cyclopentylmethyl-N-methyl-4-methoxybenzenesulfonamide |
| 26 | (cyclic carbonate-phenyl group with N-methyl amide) | cyclopentylmethyl-N-methyl-4-methoxybenzenesulfonamide |
| 27 | (aminomethyl-phenyl group with N-methyl amide) | cyclopentylmethyl-N-methyl-4-methoxybenzenesulfonamide |

TABLE 1-continued
| Cmpd. No. | A | Z |
|---|---|---|
| 28 | 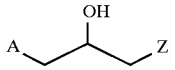 | 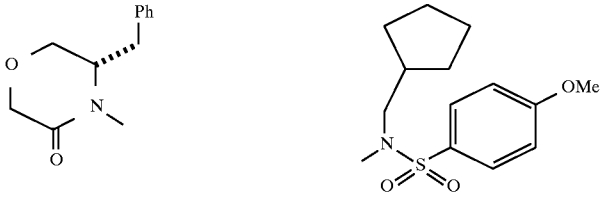 |
| 29 | 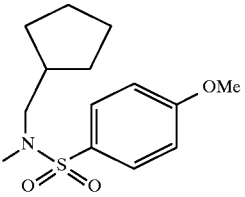 | 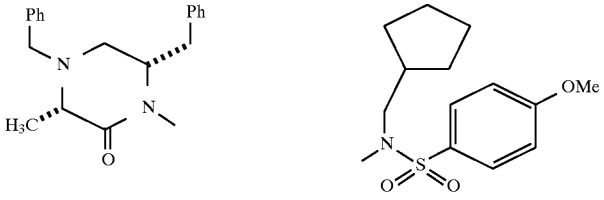 |
| 30 | 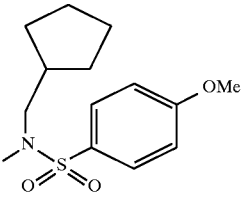 | 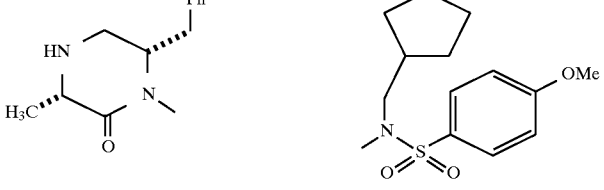 |
| 31 | 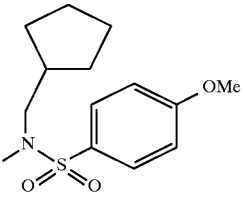 | 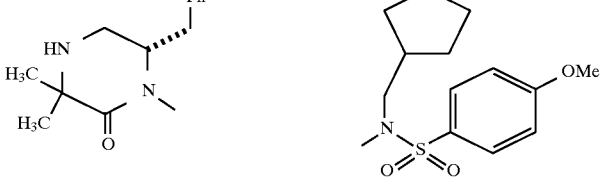 |
| 32 | 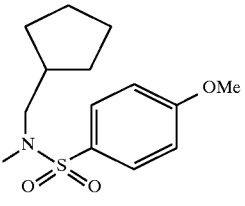 | 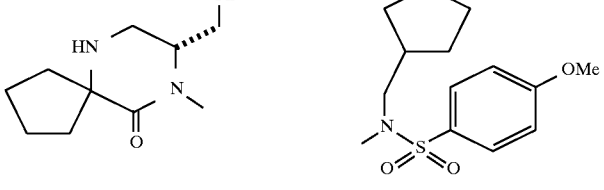 |
| 33 | 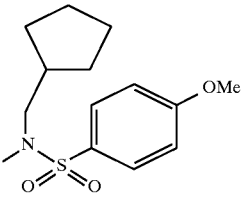 | 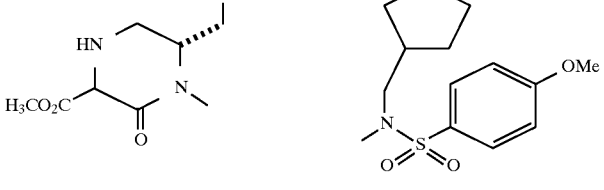 |
| 34 | 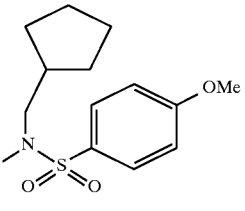 | 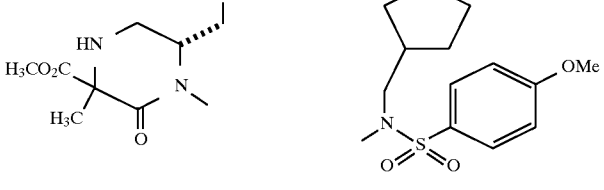 |

TABLE 1-continued $$\text{A}\diagdown\overset{\overset{\text{OH}}{|}}{\diagup}\text{Z}$$

| Cmpd. No. | A | Z |
|---|---|---|
| 35 | | |
| 36 | | |
| 37 | | |
| 38 | | |
| 39 | | |
| 40 | | |
| 41 | | |

TABLE 1-continued $$A \diagdown \overset{OH}{\diagup} Z$$

| Cmpd. No. | A | Z |
|---|---|---|
| 42 | (tetrahydropyran-2-yl)methyl-CH(CH2Ph)-C(O)-N(Me)- | -CH2-cyclopentyl, N(Me)SO2-C6H4-OMe(p) |
| 43 | HO-(CH2)3-CH(CH2Ph)-C(O)-N(Me)- | -CH2-cyclopentyl, N(Me)SO2-C6H4-OMe(p) |
| 44 | H3C-O-C(O)-CH2-CH(CH2Ph)-C(O)-N(Me)- | -CH2-cyclopentyl, N(Me)SO2-C6H4-OMe(p) |
| 45 | H2N-C(O)-CH2-CH(CH2Ph)-C(O)-N(Me)- | -CH2-cyclopentyl, N(Me)SO2-C6H4-OMe(p) |
| 46 | Ph-CH2-N(SO2)-CH2-CH(CH2Ph)-N(Me)- | -CH2-cyclopentyl, N(Me)SO2-C6H4-OMe(p) |
| 47 | (1-oxaspiro cyclohexyl)-C(O)-N(Me)-CH(CH2Ph)-CH2- | -CH2-cyclopentyl, N(Me)SO2-C6H4-OMe(p) |
| 48 | Ph-CH2-CH2-CH(CH2Ph)-N(Me)SO2- | -CH2-cyclopentyl, N(Me)SO2-C6H4-OMe(p) |

TABLE 1-continued
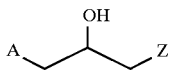

TABLE 2

| Cmpd. No. | A | R¹ | Z |
|---|---|---|---|
| 55 | allyl-N,N'-carbonyl-imidazolidine with Bn substituent | Bn | acetamido-hydroxyindane |
| 56 | HN-C(CH₃)₂-C(O)-N(CH₃)- with CH₂Ph | Bn | acetamido-hydroxyindane |
| 57 | allyl-pyrrolidinone with Bn substituent | Bn | acetamido-hydroxyindane |
| 58 | HN-cyclohexyl-C(O)-N(CH₃)- with CH₂Ph | Bn | acetamido-hydroxyindane |
| 59 | N-benzyl-N'-methyl-imidazolidinone with Bn | Bn | acetamido-hydroxyindane |
| 60 | benzyl-pyrrolidinone with Bn | Bn | acetamido-hydroxyindane |
| 61 | benzyl-sulfonamide with Bn | Bn | acetamido-hydroxyindane |

TABLE 3

[Structure: A-CH2-CH(OH)-C(=O)-Z]

| Cmpd No. | A | Z |
|---|---|---|
| 62 | [allyl-N-C(=O)-N(Me)-CH(CH2Ph)-CH2-] | [thiazolidine-CH(C(=O)NHtBu)-N(Me)-] |
| 63 | [tBu-C(NH-)-C(=O)-N(Me)-CH(CH2Ph)-CH2-] | [thiazolidine-CH(C(=O)NHtBu)-N(Me)-] |
| 64 | [allyl-CH2-CH-C(=O)-N(Me)-CH(CH2Ph)- (pyrrolidinone)] | [thiazolidine-CH(C(=O)NHtBu)-N(Me)-] |
| 65 | [cyclohexyl-spiro-NH-CH2-CH(CH2Ph)-N(Me)-C(=O)-] | [thiazolidine-CH(C(=O)NHtBu)-N(Me)-] |
| 66 | [benzyl-N-C(=O)-N(Me)-CH(CH2Ph)-CH2- (imidazolidinone)] | [thiazolidine-CH(C(=O)NHtBu)-N(Me)-] |
| 67 | [PhCH2-CH-C(=O)-N(Me)-CH(CH2Ph)- (pyrrolidinone)] | [thiazolidine-CH(C(=O)NHtBu)-N(Me)-] |
| 68 | [benzyl-CH2-CH(S(=O)2)-N(Me)-CH(CH2Ph)- (sulfonamide ring)] | [thiazolidine-CH(C(=O)NHtBu)-N(Me)-] |

TABLE 4

| Cmpd No. | A | Z |
|---|---|---|
| 69 | N-allyl, N'-methyl imidazolidinone with CH2Ph | thiazolidine-CONHtBu |
| 70 | HN-C(CH3)2-C(O)-N(Me)-CH(CH2Ph)-CH2 | thiazolidine-CONHtBu |
| 71 | allyl-substituted N-methyl pyrrolidinone with CH2Ph | thiazolidine-CONHtBu |
| 72 | 1-amino-cyclohexanecarbonyl-N(Me)-CH(CH2Ph)-CH2-NH | thiazolidine-CONHtBu |
| 73 | N-benzyl, N'-methyl imidazolidinone with CH2Ph | thiazolidine-CONHtBu |
| 74 | 3-benzyl-N-methyl pyrrolidinone with CH2Ph | thiazolidine-CONHtBu |
| 75 | benzyl-CH-S(O)2-N(Me)-CH(CH2Ph) | thiazolidine-CONHtBu |

TABLE 5

A group with OH and R¹ substituents on a chain ending in Z

| Cmpd No. | A | R¹ | Z |
|---|---|---|---|
| 76 | allyl-N-C(=O)-N(Me)-CH(CH₂Ph)-CH₂– (imidazolidinone with allyl and Ph-CH₂) | Bn | H-N(Me)-C(=O)-O-(tetrahydrofuran-3-yl)-CH₂-O |
| 77 | HN-C(=O)-C(Me)₂-... with CH₂Ph and N-Me | Bn | H-N(Me)-C(=O)-O-(tetrahydrofuran-3-yl)-CH₂-O |
| 78 | allyl-CH-C(=O)-N(Me)-CH(CH₂Ph)- (pyrrolidinone with allyl) | Bn | H-N(Me)-C(=O)-O-(tetrahydrofuran-3-yl)-CH₂-O |
| 79 | HN-C(cyclohexyl)-C(=O)-N(Me)-CH(CH₂Ph)- | Bn | H-N(Me)-C(=O)-O-(tetrahydrofuran-3-yl)-CH₂-O |
| 80 | PhCH₂-N-C(=O)-N(Me)-CH(CH₂Ph)- (imidazolidinone with benzyl) | Bn | H-N(Me)-C(=O)-O-(tetrahydrofuran-3-yl)-CH₂-O |
| 81 | PhCH₂-CH-C(=O)-N(Me)-CH(CH₂Ph)- (pyrrolidinone with benzyl) | Bn | H-N(Me)-C(=O)-O-(tetrahydrofuran-3-yl)-CH₂-O |
| 82 | PhCH₂-CH-S(=O)₂-N(Me)-CH(CH₂Ph)- (sulfonamide ring) | Bn | H-N(Me)-C(=O)-O-(tetrahydrofuran-3-yl)-CH₂-O |

The preferred compounds of this invention are compound numbers: 1, 2, 3, 4, 7, 8, 9, 13, 14, 16, 17, 18, 20, 23, 24, 25, 26, 32, 35, 38, 44, 45, 46, 47, 48, 49, 50, 51, 52, 53, 54, 59, 60, 66, 67, 81 and 82. More preferred are compound numbers: 2, 7, 8, 9, 14, 18, 20, 25, 26, 32, 38, 45, 47, 48, 49, 50, 51, 52 and 53. Even more preferred are compound numbers: 7, 8, 9, 20, 45, 50, 51, 52 and 53.

The compounds of this invention may be synthesized using conventional techniques. Advantageously, these compounds are conveniently synthesized from readily available starting materials.

Although the syntheses of the compounds of this invention are known to those of skill in the art, the following general schemes are set forth to illustrate these methods. These schemes should not be viewed as limiting the scope of this invention in any way.

Using standard techniques, compounds of the present invention having the general formula I may be obtained as described in the following schemes:

SCHEME 1
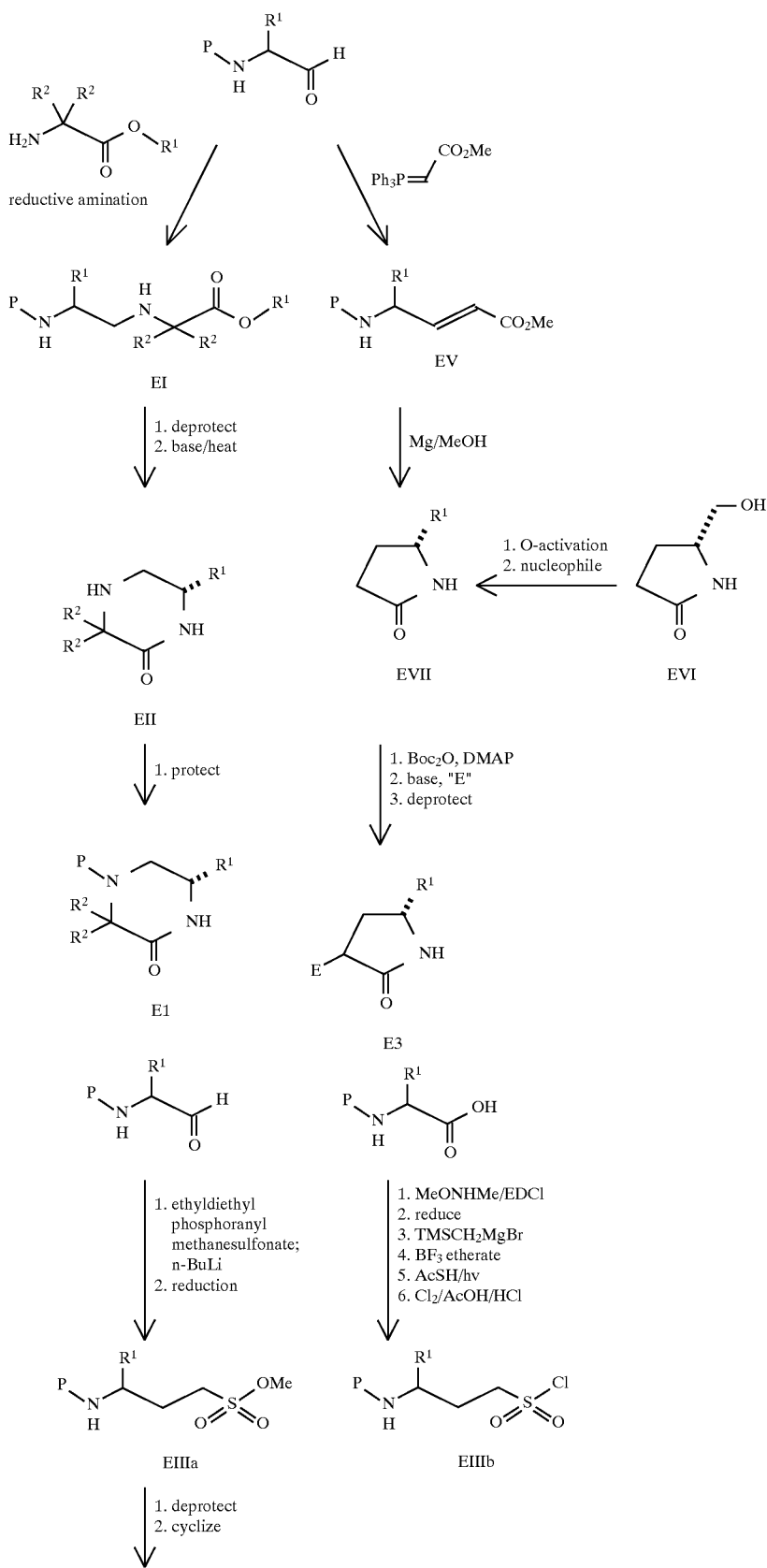

-continued
SCHEME 1
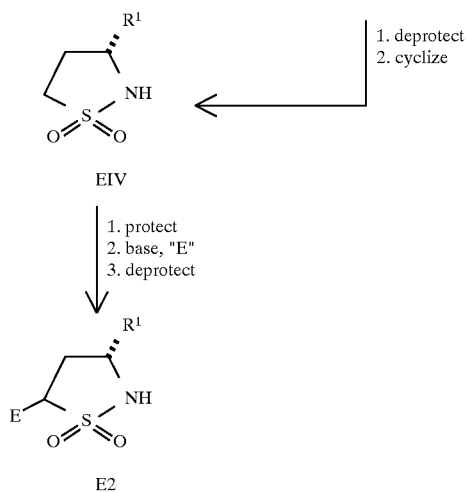
SCHEME 2
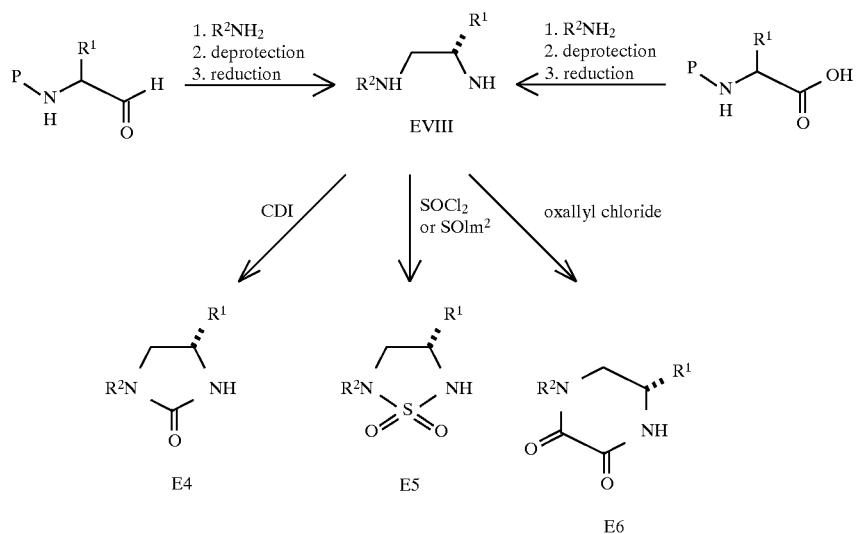
SCHEME 3
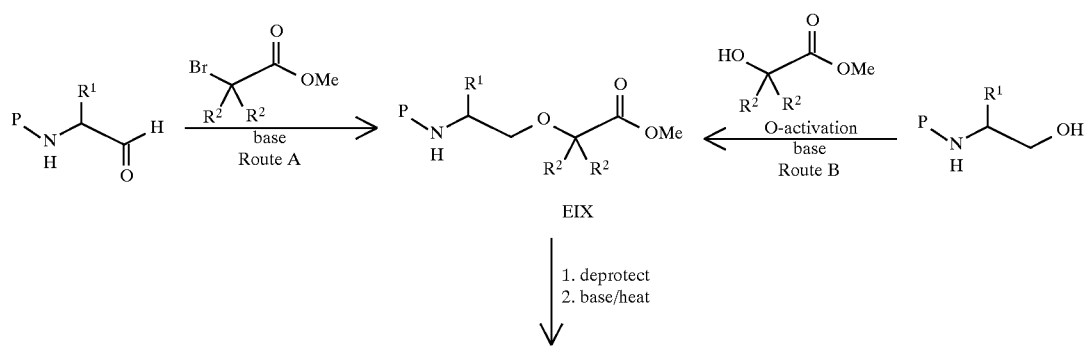

-continued
SCHEME 3
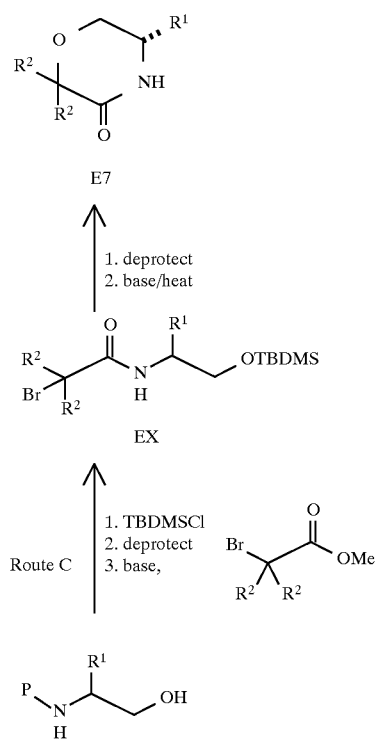
SCHEME IV
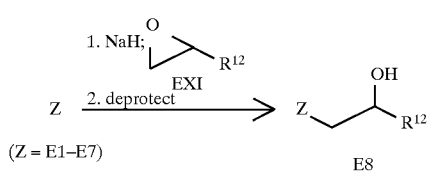
(Z = E1–E7)
R[12] =
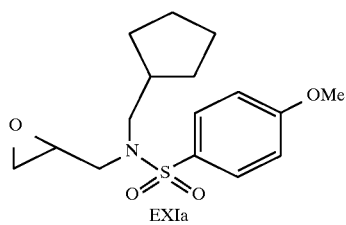
-continued
SCHEME IV
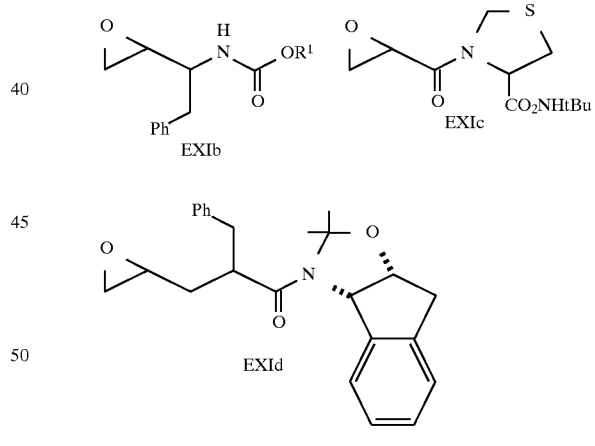

SCHEME 5

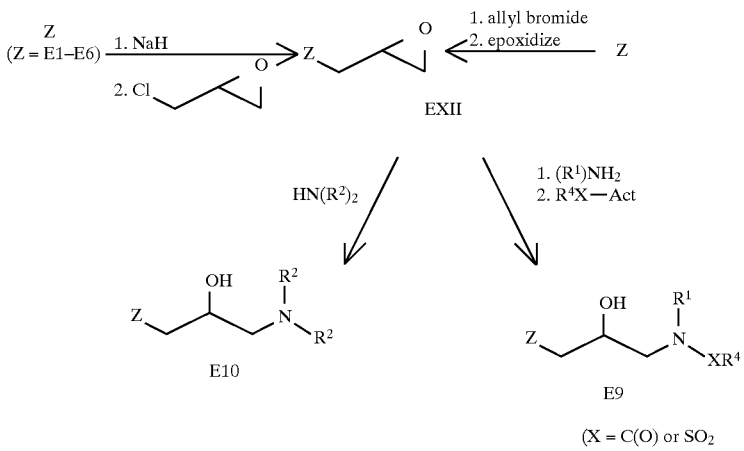

SCHEME 6

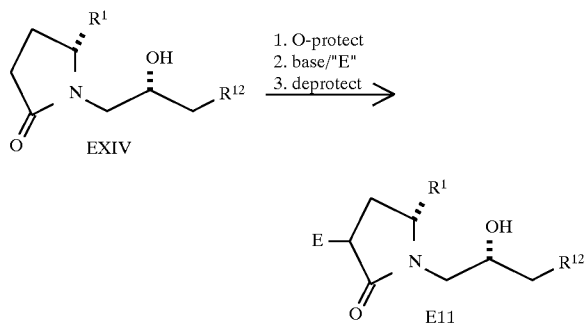

Methods for producing the compounds of this invention are well known in the art of organic synthesis. Several intermediates are commercially available, e.g. from Aldrich Chemical Company, Inc., Milwaukee, Wis. The synthesis of heterocycles E1–E6 (Schemes 1 and 2) begins with any protected amino aldehyde, the preparations for which are well known in the art from suitably protected amino acids, esters or alcohols. In the case of the this intermediate, transient protection of the amino group may be accomplished by means known in the art (see, e.g. T. W. Greene and P. G. M. Wuts "Protective Groups in Organic Synthesis", Second Edition, pp. 309–405 ©1991 John Wiley and Sons, Inc. New York, N.Y. and E. Gross and J. Meinhofer "The Peptides, Vol. 3: Protection of Functional Groups in Peptide Synthesis" pp. 3–88; ©1981 Academic Press, Inc. New York, N.Y.). Carbamates such as Boc, Fmoc, Alloc and Cbz are particularly convenient protecting groups, the introduction and removal of are described in the above references.

The synthesis of E1 is illustrated in Scheme 1. The protected amino aldehyde is treated with an alpha substituted or alpha, alpha disubstituted amino ester under typical reductive amination conditions well known in the art, such as sodium cyanoborohydride in a solvent mixture of DMF/Acetic acid. The resulting compound EI is then deprotected and free based with either a tertiary amine base or potassium carbonate in methanol to effect cyclization to form EII The resulting secondary amine may the be protected with groups (detailed in the references above) such as benzyl or t-butyloxycarbonyl (Boc) utilizing conditions well known in the art to form analogs of E1.

Preparation of E2 is achieved by reaction of a starting aldehyde with ethyl diethylphosphoranylmethanesulfonate and subsequent reduction of the double bond (see: Gennari et al., *Angew. Chem. Int. Ed. Engl.*, 33, pp. 2067–69 (1994)) to yield compound EIIIa. Cyclization may then be achieved by deesterification and activation of the sulfonate moiety as described in Gennari, followed by deprotection of the nitrogen protection group to yield the cyclized product EIV. Alternatively, an amino acid may be converted to compound EIIIb using standard synthetic methods illustrated in Scheme 1. Compound EIIIb can be cyclized to afford compound EIV. Compound EIV may then be N-protected, for example, in the presence of Boc anhydride and DMAP (see: Flynn et al., *J. Org. Chem.* 48, pp. 2424–26 (1983)), and treated with a non-nucleophilic base such as LDA or hexamethyldisilazane to generate the anion at the center alpha to the $SO_2$ moiety. This anion may then be quenched with a variety of electrophiles and subsequently deprotected to form the desired analogs of E2. Analogously, preparation of E3 results from a Wittig reaction using methyl(triphenylposphoranylidene) acetate followed by simultaneous reduction of the double bond and cyclization using magnesium metal in methanol (Wei et al., *Tetrahedron Lett.*, 34(28), pp. 4439–42 (1993)). A similar N-protection, deprotonation, quench and N-deprotection scheme as described in the preparation of E2, results in desired analogs of E3. Alternatively, E3 may be prepared from commercially available EVI. The hydroxyl group may be activated using commonly available reagents such as methanesulfonyl chloride or para-toluenesulfonyl chloride in the presence of a tertiary amine base. The addition of a nucleophile to displace the mesylate or tosylate yields EVII (Ackermann et al., *Helv. Chim. Acta*, 73, pp. 122–32 (1990)) which may be treated as described above to obtain E3.

Methods for the preparation of compounds E4–E6 are also well known in the art and stem from readily available protected amino aldehydes. Treatment of these aldehydes with a variety of amines under reductive amination conditions well known in the art, such as sodium cyanoborohydride using DMF/Acetic acid as a solvent mixture, followed by deprotection of the primary amine yields diamine EVIII. Intramolecular cyclization with a variety of activated carbonyl, dicarbonyl or sulfuryl equivalents in the presence of a tertiary amine base yields compounds E4–E6. Examples of activating reagents include but are not limited to carbonyldiimidazole, phosgene, sulfuryldichloride, sulfuryldiimidazole, sulfonyl diimide, and oxalyl chloride.

Methods leading to the production of analogs of compound E7 are also known in the art (McManus et al., *J. Med. Chem.*, 8, pp. 766–76 (1965)). Scheme 3 exemplifies several potential routes to the synthesis of compound E7. Any protected amino alcohol may be deprotonated to form the alkoxide which may be reacted with a substituted alpha bromo ester to form ether EIX (route A). Alternatively (route B), EIX may be formed from activation of a protected amino alcohol with, for example, methanesulfonyl chloride or paratoluenesulfonyl chloride in the presence on a tertiary amine base and subsequent addition of a nucleophile such as an alkoxide from an alpha hydroxy acid to displace mesylate or tosylate to yield EIX. Compound EIX can then be deprotected, free based with a tertiary amine base or potassium carbonate in methanol, and heated to effect cyclization to form E7. Alternatively (route C), E7 may be prepared from a protected amino alcohol by protection of the hydroxyl group with, for example, t-butyldimethyl silyl chloride/imidazole to afford the silyl ether. Subsequent nitrogen deprotection and acylation with a alpha bromo acid in the presence of any number of available coupling agents (for example dicylcohexylcarbodiimide, other related carbodiimide reagents or isobutyl chloroformate) or acylation with an alpha bromo acid chloride provides compound EX. Desilylation using, for example, tetrabutylammonium formate in THF followed by formation of the alkoxide with base affords cyclization to E7.

Schemes 4–6 describe methods for converting the cyclic compounds E1–E7 into compounds of this invention. For example, compounds of the type Z, exemplified by compounds E1–E7, may be deprotonated and reacted with a functionalized epoxide to generate the desired compounds as described in Scheme 4. Several of the described epoxides are readily synthesized via methods well known in the art (Maligres et al, *Tetrahedron Lett.*, 36, pp. 2195–98 (1995)). Optionally, further modification of the compounds may be performed subsequent to epoxide opening using reactions and materials well known in the art. For example, subsequent to epoxide opening utilizing example EXIb deprotection of the carbamate allows further modification of the unmasked amine.

Alternatively, as shown in Scheme 5, compounds EZ may be converted to the desired products in a more stepwise fashion. Compounds EZ may be deprotonated using, for example, sodium hydride in DMF and treated with a three carbon based epoxide to generate epoxide EXII. Examples of such reagents include, but are not limited to, epibromohydrin, epichlorohydrin and glycidyl tosylate. Several other potential methods for preparing compounds of the type EXII are well known in the art, for example, the anion of Z may be reacted with allyl bromide or allyl iodide to form an allyl intermediate, which may subsequently be oxidized to form the desired epoxide. Several epoxidation conditions for the generation of either racemic or chiral epoxides are well known in the art. Epoxide EXII may then be treated with an amine and susequently carbonylated or sulfonated using activated species well known in the art to generate final compounds of the type E9. Alternatively EXII may be reacted with a functionalized secondary amine followed by optional manipulation of $R^2$ to produce compounds of the type E10. One example of such manipulation is reaction of EXII with the known Boc piperazine EXIII (Dorsey et al., *J. Med. Chem.*, 37, pp. 3443–51 (1994)). Subsequent to epoxide opening, the Boc group may be removed and the unmasked secondary amine may be further manipulated by reaction with various electrophiles to form the desired product.

Scheme 6 describes a method for introduction of electrophiles into compounds of the type EXIV. Said compounds may be protected with a variety of protecting groups, for example t-butyldimethylsilyl triflate, to mask the secondary hydroxyl group followed by treatment with a non-nucleophilic base such as lithium diisopropylamide or hexamethyldisilyzane to generate the anion alpha to the carbonyl. Various electrophiles may then be added to substitute the position alpha to the carbonyl. Deprotection of the secondary hydroxyl then yields the desired product.

As can be appreciated by the skilled artisan, the above synthetic schemes are not intended to comprise a comprehensive list of all means by which the compounds described and claimed in this application may be synthesized. Further methods will be evident to those of ordinary skill in the art.

It should be understood that the compounds of this invention may be modified by appending appropriate functionalities to enhance selective biological properties. Such modifications are known in the art and include those which increase biological penetration into a given biological compartment (e.g., blood, lymphatic system, central nervous system), increase oral availability, increase solubility to allow administration by injection, alter metabolism and alter rate of excretion.

The compounds of this invention are characterized by a superior ability to inhibit protease activity and viral replication, particularly aspartyl protease activity. These compounds are especially well suited for inhibiting HIV aspartyl protease. We believe that this activity is due to specific steric and electronic interactions between the protease and compounds of this invention. This belief stems from our analysis of the structural basis for the activity of compounds of this invention, in view of the known crystal structures of HIV protease and bound inhibitors, such as the structure reported in Miller et al. "Structure of Complex of Synthetic HIV-1 Protease with a Substrate-Based Inhibitor at 2.3 Å Resolution", *Science*, vol. 246, pp. 1149–1152 (1989), which is incorporated herein by reference, as well as structures determined in our laboratories.

The novel compounds of the present invention are excellent ligands for aspartyl proteases, particularly HIV-1 and HIV-2 proteases. Accordingly, these compounds are capable of targeting and inhibiting late stage events in HIV replication, i.e., the processing of the viral polyproteins by HIV encoded proteases. Such compounds inhibit the proteolytic processing of viral polyprotein precursors by inhibiting aspartyl protease. Because aspartyl protease is essential for the production of mature virions, inhibition of that processing effectively blocks the spread of virus by inhibiting the production of infectious virions, particularly from chronically infected cells. Compounds according to this invention advantageously inhibit the ability of the HIV-1 virus to infect immortalized human T cells over a period of days, as determined by an assay of extracellular p24 antigen—a specific marker of viral replication. Other antiviral assays have confirmed the potency of these compounds.

The compounds of this invention may be employed in a conventional manner for the treatment of viruses, such as HIV and HTLV, which depend on aspartyl proteases for obligatory events in their life cycle. Such methods of treatment, their dosage levels and requirements may be selected by those of ordinary skill in the art from available methods and techniques. For example, a compound of this invention may be combined with a pharmaceutically acceptable adjuvant for administration to a virally-infected patient in a pharmaceutically acceptable manner and in an amount effective to lessen the severity of the viral infection or to alleviate pathological effects associated with HIV infection or immunosuppression such as opportunistic infections or various cancers, tumors, CMV retinitis, candida infections, maternal fetal transmission, and AIDS related dementia,.

Alternatively, the compounds of this invention may be used in prophylactics and methods for protecting individuals against viral infection during a specific event, such as childbirth, or over an extended period of time. The compounds may be employed in such prophylactics either alone or together with other antiretroviral agents to enhance the efficacy of each agent. As such, the novel protease inhibitors of this invention can be administered as agents for treating or preventing HIV infection in a mammal.

The compounds of formula I, especially those having a molecular weight of less than about 700 g/mole, may be readily absorbed into the bloodstream of mammals upon oral administration. Compounds of formula I having a molecular weight of less than about 600 g/mole and aqueous solubility of greater than or equal to 0.1 mg/mL are most likely to demonstrate high and consistent oral availability. This surprisingly impressive oral availability makes such compounds excellent agents for orally-administered treatment and prevention regimens against HIV infection.

The compounds of this invention may be administered to a healthy or HIV-infected patient either as a single agent or in combination with other anti-viral agents which interfere with the replication cycle of HIV. By administering the compounds of this invention with other anti-viral agents which target different events in the viral life cycle, the therapeutic effect of these compounds is potentiated. For instance, the co-administered anti-viral agent can be one which targets early events in the life cycle of the virus, such as cell entry, reverse transcription and viral DNA integration into cellular DNA. Anti-HIV agents targeting such early life cycle events include, didanosine (ddI), dideoxycytidine (ddC), d4T, zidovudine (AZT), 3TC, 935U83, 1592U89, 524W91, polysulfated polysaccharides, sT4 (soluble CD4), ganiclovir, trisodium phosphonoformate, eflornithine, ribavirin, acyclovir, alpha interferon and trimethotrexate. Additionally, non-nucleoside inhibitors of reverse transcriptase, delavirdine (U90) or nevirapine, may be used to potentiate the effect of the compounds of this invention, as may viral uncoating inhibitors, inhibitors of trans-activating proteins such as tat or rev, or inhibitors of the viral integrase.

Combination therapies according to this invention exert an additive or synergistic effect in inhibiting HIV replication because each component agent of the combination acts on a different site of HIV replication. The use of such combination therapies may also advantageously reduce the dosage of a given conventional anti-retroviral agent which would be required for a desired therapeutic or prophylactic effect, as compared to when that agent is administered as a monotherapy. Such combinations may reduce or eliminate the side effects of conventional single anti-retroviral agent therapies, while not interfering with the anti-retroviral activity of those agents. These combinations reduce potential of resistance to single agent therapies, while minimizing any associated toxicity.

Advantages of combining HIV protease inhibitors may include viral population effects, whereby certain members of a virus population which show reduced sensitivity to one protease inhibitor may be fully sensitive to another inhibitor or may in fact have enhanced sensitivity to the second inhibitor. Alternatively or in addition, administration of two or more different inhibitors may be used to reduce specific toxicities associated with a single agent. This advantage of combination therapy also applies to co-administration of the protease inhibitor of this invention with other antiviral agents. Alternatively or in addition, co-administration of more than one protease inhibitor may lower the rate of metabolic inactivation of the compounds of this invention, for instance, by inhibiting enzymatic systems such as cytochrome $P_{450}$, or esterases or the like. In particular, co-administration of compounds of this invention with protease inhibitors such as ritonavir or other agents such as ketoconazole, which inhibits cytochrome $P_{450}$ $3A_4$, may advantageously enhance their biological half-life.

These combinations may also increase the efficacy of the conventional agent without increasing the associated toxicity. Compounds of this invention in combination with other anti-HIV agents may act in an additive or synergistical manner in preventing the replication of HIV in human T cells. Preferred combination therapies include the administration of a compound of this invention with AZT, ddI, ddC, d4T, 3TC, 935U83, 1592U89, 524W91 or a combination thereof.

Alternatively, the compounds of this invention may also be co-administered with other HIV protease inhibitors such as saquinavir (Ro 31-8959, Roche), indinavir (L-735,524, Merck)), ritonavir (ABT 538, Abbott), nelfinavir (AG 1343, Agouron), palinavir (Bila 2011 BS), U103017 (Upjohn), XM 412 (DuPont Merck), XM 450 (DuPont Merck), BMS 186318 (Bristol-Meyers Squibb) and CPG 53,437 (Ciba Geigy) or prodrugs of these or related compounds to increase the effect of therapy or prophylaxis against various viral mutants or members of HIV quasi species.

We prefer administering the compounds of this invention as single agents or in combination with retroviral reverse transcriptase inhibitors, such as nucleoside derivatives, or other HIV aspartyl protease inhibitors, including multiple combinations comprising from 3–5 agents. We believe that the co-administration of the compounds of this invention with retroviral reverse transcriptase inhibitors or HIV aspartyl protease inhibitors may exert a substantial additive or synergistic effect, thereby preventing, substantially reducing, or completely eliminating viral replication or infection or both, and symptoms associated therewith. Particularly preferred is administration of a combination of a compound of formula I, 3TC and zidovudine (AZT).

The compounds of this invention can also be administered in combination with immunomodulators and immunostimulators (e.g., bropirimine, anti-human alpha interferon antibody, IL-2, GM-CSF, interferon alpha, diethyldithiocarbamate, tumor necrosis factor, naltrexone, tuscarasol, and rEPO); and antibiotics (e.g., pentamidine isethiorate) to prevent or combat infection and disease associated with HIV infections, such as AIDS, ARC and HIV-associated cancers.

When the compounds of this invention are administered in combination therapies with other agents, they may be administered sequentially or concurrently to the patient. Alternatively, pharmaceutical compositions according to this invention may comprise a combination of an aspartyl protease inhibitor of this invention and one or more therapeutic or prophylactic agents.

Although this invention focuses on the use of the compounds disclosed herein for preventing and treating HIV infection, the compounds of this invention can also be used as inhibitory agents for other viruses which depend on similar aspartyl proteases for obligatory events in their life cycle. These viruses include other AIDS-like diseases caused by retroviruses, such as simian immunodeficiency viruses, HTLV-I and HTLV-II. In addition, the compounds of this invention may also be used to inhibit other aspartyl proteases, such as renin, pepsin, cymosin, RSV protease, AMV protease, SIV protease and FIV protease, and in particular, other human aspartyl proteases, including renin, and aspartyl proteases that process endothelin precursors.

Pharmaceutical compositions of this invention comprise any of the compounds of the present invention, and pharmaceutically acceptable salts thereof, with any pharmaceutically acceptable carrier, adjuvant or vehicle. Pharmaceutically acceptable carriers, adjuvants and vehicles that may be used in the pharmaceutical compositions of this invention include, but are not limited to, ion exchangers, alumina, aluminum stearate, lecithin, self-emulsifying drug delivery systems (SEDDS) such as d-α-tocopherol polyethyleneglycol 1000 succinate, serum proteins, such as human serum albumin, polyethyleneglycol polymers such as PEG-400, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solublized derivatives may also be advantageously used to enhance delivery of compounds of formula I.

The pharmaceutical compositions of this invention may be administered orally, parenterally, by inhalation spray, topically, rectally, nasally, buccally, vaginally or via an implanted reservoir. We prefer oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant such as Ph. Helv or a similar alcohol.

The pharmaceutical compositions of this invention may be orally administered in any orally acceptable dosage form including, but not limited to, hard or soft gelatin capsules, tablets, and aqueous suspensions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavoring and/or coloring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions of this invention is especially useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-transdermal patches are also included in this invention.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

Dosage levels of between about 0.01 and about 100 mg/kg body weight per day, preferably between about 0.5 and about 75 mg/kg body weight per day of the active ingredient compound are useful in the prevention and treatment of viral infection, including HIV infection. Typically, the pharmaceutical compositions of this invention will be administered from about 1 to about 5 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. Patients may, however, require intermittent treatment on a long-term basis upon any recurrence of disease symptoms.

As the skilled artisan will appreciate, lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the infection, the patient's disposition to the infection and the judgment of the treating physician.

The compounds of this invention are also useful as commercial reagents which effectively bind to aspartyl proteases, particularly HIV aspartyl protease. As commercial reagents, the compounds of this invention, and their derivatives, may be used to block proteolysis of a target peptide or may be derivatized to bind to a stable resin as a tethered substrate for affinity chromatography applications. For example, a compound of formula I may be tethered to an affinity column to purify recombinantly produced HIV protease. Derivatization of the compounds of this invention to produce affinity chromatography resins and the methods used to purify proteases using such resins are well known and within the skill of the art. These and other uses which characterize commercial aspartyl protease inhibitors will be evident to those of ordinary skill in the art. (See: Rittenhouse, J. et al. Biochem. Biophys. Res. Commun. 171, p. 60 (1990) and Heimbach, J. C. et al. Ibid 164, p. 955 (1989)).

In order that this invention be more fully understood, the following examples are set forth. These examples are for the purpose of illustration only and are not to be construed as limiting the scope of the invention in any way.

General Materials and Methods

All temperatures are recorded in degrees Celsius. Thin layer chromatography (TLC) was carried out using 0.25 mm thick E. Merck silica gel 60 $F_{254}$ plates and elution with the indicated solvent system. Detection of the compounds was carried out by treating the plate with an appropriate visualizing agent, such as 10% solution of phosphomolybdic acid in ethanol or a 0.1% solution of ninhydrin in ethanol, followed by heating, and/or by exposure to UV light or iodine vapors when appropriate. Thick layer silica gel chromatography was also carried out using E. Merck 60 $F_{254}$ plates ("prep plates") of 0.5, 1.0, or 2.0 mm thickness. Following development of the plate, the band of silica containing the desired compound was isolated and eluted with an appropriate solvent. Analytical HPLC was carried out using a Water's Delta Pak, 5 $\mu$M silica, C18 reversed-phase column, 3.9 mm ID×15 cm L with a flow rate of 1.5 mL/min using the following table:

Mobile phase: A=0.1% $CF_3CO_2H$ in $H_2O$
B=0.1% $CF_3CO_2H$ in $CH_3CN$
Gradient: T=0 min., A (95%), B (5%)
T=20 min., A (0%), B (100%)
T=22.5 min., A (0%), B (100%)

Preparative HPLC was also carried out using $C_{18}$ reversed-phase media. HPLC retention times were recorded in minutes. NMR spectral data was recorded using a Bruker AMX500, equipped with either a reverse or QNP probe, at 500 MHz, and was taken in the indicated solvent.

We have measured the inhibition constants of each compound against HIV-1 protease using the method described essentially by M. W. Pennington et al., Peptides 1990, Gimet, E. and D. Andrew, Eds., Escom; Leiden, Netherlands (1990).

Compounds of invention were tested for their antiviral potency in several virological assays. In the first assay, the compounds were added as a solution in dimethylsulfoxide (DMSO) to a test cell culture of CCRM-CEM cells, a strain of $CD4^+$ human T-cell lymphoma cells, previously acutely infected with $HIV_{IIIb}$ using standard protocols (see Meek, T. D. et al., "Inhibition of HIV-1 protease in infected T-lymphocytes by synthetic peptide analogues", Nature, 343, p. 90 (1990).

The effect of the compounds on inhibiting the replication of the virus was measured by determining the HIV extracellular p24 antigen concentration using a commercial enzyme immunoassay (obtained from Coulter Corporation, Hialeah, Fla.).

Depending on the cell type and the desired readout, syncytia formation, reverse-transcriptase (RT) activity, or cytopathic effect as assayed by a dye uptake method may also be used as readouts of antiviral activity. See H. Mitsuya and S. Broder, "Inhibition of the in vitro infectivity and cytopathic effect of human T-lymphotropic virus type III/lymphoadenopathy-associated virus (HTLV-III/LAV) by 2', 3'-dideoxynucleosides", Proc. Natl. Acad. Sci. USA, vol. 83, pp. 1911–1915 (1986).

Insofar as the compounds of this invention are able to inhibit the replication of the HIV virus in $CD_4^+$ cells of human lineage, they are of evident clinical utility for the treatment of HIV infection. These tests are predictive of the compounds ability to inhibit HIV protease in vivo.

SYNTHETIC EXAMPLES

Example 1

A.

| | | | |
|---|---|---|---|
| N-(t-butoxycarbonyl)-L-phenylalaninol; | 251.3 g/Mol | 10.0 g | 39.8 mmol |
| DMSO | 78 g/Mol | 3.80 mL | 49.0 mmol |
| oxalyl chloride | 126.9 g/Mol | 3.82 mL | 43.8 mmol |
| triethylamine | 101 g/Mol | 23.0 mL | 160 mmol |
| methylene chloride | | 200 mL | |

The oxalyl chloride was added dropwise to a solution of DMSO in methylene chloride at −78° C. After stirring for 10 minutes, the alcohol was added as a solution in methylene chloride. The reaction was then stirred at −78° C. for 45 minutes. At this time the triethylamine was added and a white precipitate formed. The reaction was then stirred 45 minutes at −78° C. and 45 minutes at 0° C. The reaction was then quenched by the addition of a solution of 90 g of citric acid in 300 mL of water. The organic portion of the reaction was then washed by (2×80 mL) of both saturated sodium bicarbonate and brine. The combined organic layers were then dried over sodium sulfate, filtered and concentrated in vacuo to leave a white solid. The aldehyde was then used without further purification in the reductive amination.

| B. | | | |
|---|---|---|---|
| allyl amine | 57 g/Mol | 6.0 mL | 160 mmol |
| aldehyde | | | est. 39.8 mmol |
| sodium cyanoborohydride | 62.8 g/Mol | 4.0 g | 6.4 mmol |
| DMF | | | 180 mL |
| acetic acid (glacial) | | | 1.8 mL |

The aldehyde of Example 1A was dissolved in 180 mL of DMF at 25° C. This was followed by addition of the aldehyde and 1.8 mL of acetic acid respectively. After 2 hours sodium cyanoborohydride was added, as a solid. The reaction was then stirred at 25° C. for 12 hours. The reaction was then quenched by the addition of 50 mL of saturated sodium bicarbonate, and after 10 min. diluted by 100 mL of diethyl ether. The organic portion was then washed by (2×50 mL) of both saturated sodium bicarbonate and brine. The combined organic layers were then dried over magnesium sulfate, filtered and concentrated in vacuo. The crude oil was purified by silica gel chromatography eluting with 30% ethyl acetate: hexane to provide 8.8 g of product (29.8 mmol, 75%).

| C. | | | |
|---|---|---|---|
| Boc amine | 291 g/Mol | 6.8 g | 23.4 mmol |
| Hcl/dioxane | 4 N Hcl | 15 mL | |
| deprotected diamine-2HCl | | 3.83 g | 14.7 mmol |
| carbonyl diimidazole | 162.15 g/Mol | 2.77 g | 17.1 mmol |
| triethylamine | | 12.7 mL | 179 mmol |
| methylene chloride | | 550 mL | 0.03 M |

The Boc amine of Example 1B was stirred in 15 mL of 4N HCl at 25° C. for 1.5 hours. The reaction mixture was then concentrated in vacuo to provide a white foaming solid. 3.83 mg of the deprotected diamine was dissolved in 500 mL of methylene chloride. To this, triethyl amine was added. After stirring for 20 minutes, CDI was added (solid). The reaction was then stirred for 24 hours. his was followed by concentration in vacuo. The crude material was purified by silica gel chromatography, eluting with ethyl acetate, to provide 2.15 g (67 %) of the desired allyl urea.

| D. | | | |
|---|---|---|---|
| allyl urea | 216 g/Mol | 100 mg | 0.46 mmol |
| NaH, (60% in oil) | 24 g/Mol | 140.0 mg | 9.7 mmol |
| epoxide | 325.4 g/Mol | 150.0 mg | 0.46 mmol |
| DMF | | | 2.0 mL |

The urea of Example 1C was dissolved in 1.0 mL of anhydrous DMF and cooled to 0° C. This was followed by the addition of 140 mg NaH. The reaction turned darker over the next hour at 0° C. This was followed by the dropwise addition of the epoxide as a solution in DMF (0.6 mL), washing with 300 uL of DMF. The reaction was then stirred one hour at 0° C., followed by warming to 25° C. Tlc indicated nearly complete conversion to two new products (Rf=0.4 and 0.45 on $SiO_2$ with 2:1 hexane: ethyl acetate, between that of the epoxide and the urea). The reaction was then cooled to 25° C. and quenched by the addition of 3 mL of saturated sodium bicarbonate. The reaction mixture was then diluted by 15 mL of methylene chloride and washed by both saturated sodium bicarbonate and brine, (2×15 mL each). The organic portions were then dried over sodium sulfate, filtered and concentrated in vacuo. The crude product was then purified by silica gel chromatography, eluting with 80% ethyl acetate: hexane to provide 35.0 mg of the desired alcohol.

Example 2

| A. | | |
|---|---|---|
| 1 | aldehyde | 1.0 equiv., |
| 2 | methyl (triphenylphosphoranylidene)acetate | 1.05 eq. |
| 3 | toluene | 80 mL |
| 4 | methylene chloride | 120 mL |

Combine 7.9 g of (S)-N-Boc-amino-3-phenyl-1-propanal, 40 mL of anhydrous toluene and 60 mL of anhydrous methylene chloride. Add 9.8 g of the ylide followed by 20 mL of toluene and 60 mL of methylene chloride. Stir overnight at room temperature. After approximatly 18 hours the solvent was removed in vacuo and the residue was purified by flash chromatography (EtOAc/Hexane) to give 7.1 g(77%) of the desired ester

| B. | | |
|---|---|---|
| 1 | ester from 2A | 4.5 g, 1.0 equiv. |
| 2 | magnesium turnings | 3.2 g 10.0 eq. |
| 3 | 2N HCl | @ 10 eq. |

To a solution of 1 in anhy. methanol at 0° C. is added 2 with stirring under $N_2$. Bubbling evident within 1 hour. Stirred at 0° C. for ~2.5 hours then allowed to warm to RT overnight. The reaction was heated to 25°–30° C. for 2 hours TLC (95:5, $CH_2Cl_2$:MeOH) showed reaction complete. st. mat. Rf=0.84, prod. Rf=0.25, benzyl alcohol Rf=0.50 The reaction was cooled to 0° C., neutralized with 2N HCl , diluted with water, and the volume reduced in vacuo., extract with 3 portions of $CH_2Cl_2$ Wash comb. organics with brine, dry $MgSO_4$, filter, concentrate in vacuo. purified by flash chrom. $CH_2Cl_2 \rightarrow 3\%$ MeOH/$CH_2Cl_2$ to give 1.74 g, (75% yield)

Literature reference: *Tett. Lett.*, 1993, 34, (28), 4439–4442

| C. | | |
|---|---|---|
| 1 | lactam from 2B | 1.0 eq., 1.17 g |
| 2 | Boc anhydride | 2.5 eq., 5.2 g |
| 3 | triethylamine | 2.0 eq., 2.7 mL |
| 4 | DMAP/$CH_2Cl_2$ | 20 mL |

Dissolve 1 in 20 ml $CH_2Cl_2$. Add solution of 3 in 20 ml $CH_2Cl_2$ followed by 2.0 ml of 3 and 1.4 g of 4. After stirrring 4 hours at rt, the reaction was refluxed for 4 hours. An additional 1 g of 2 and 700 ml of 3 was added in 20 ml of acetonitrile. Cool to rt and stir for 15 hours. TLC (95:5, $CH_2Cl_2$:MeOH) Rf=0.66. The solvent was removed in vacuo and the residue partitioned between $CH_2Cl_2$ and sat'd bicarbonate solution. The aqueous phase was extracted with $CH_2Cl_2$. The combined organics were washed with water, brine, dried over MgSO4, and concentrated, and triturated with ether. Purification by chromatography $CH_2Cl_2$ gave 2.3 g (86%) of N-Boc lactam.

| D. | | |
|---|---|---|
| 1 | BOC-lactam from 2C | 1.0 eq., 85 mg |
| 2 | Allyl Bromide | 1.8 eq., 51 uL |
| 3 | LDA, 1.29M | 2.0 eq., 420 uL |

Dissolve 1 in THF. Cool to −78° C. Add 3 via syringe. After stirring for 40 min. at −78° C., 34 uL of 2 was added via syringe. After ~3 hours an additional 17 ul of 2 was added. Stirred at −78° C. for 4 hours. TLC (5:95, MeOH:CH$_2$Cl$_2$) Rf (st mat.)=0.34. Rf(2 diast.)=0.55 and 0.61 Quenched with 1 mL sat'd NHCl sol'n. Partition bet. sat'd bicarb sol'n./EtOAc. Extract aq. with EtOAc. Wash comb. organics with water, brine, dry MgSO$_4$, filter, concentrate in vacuo. Purified by chrom., 5% MeOH/CH$_2$Cl$_2$ to give 47 mg(48% yield) of allyl lactam.

Example 3

| A. | | |
|---|---|---|
| 1 | lactam | 1.0 equiv., 295 mg |
| 2 | sulfonamide epoxide | 1.1 equiv., 520 mg |
| 3 | NaH, 60% in oil | 1.5 equiv, 102 mg |
| 4 | DMF | 8 mL |

Dissolve 1 in 3 mL of DMF. Cool to ~0° C. Add 3 as a solid. After stirring for 40 min. at 0° C., the anion solution was canulated into a solution of 2 in 3 mL of DMF. Washed in with 2×1 mL of DMF. Stir at 0° C. for 5 min., then warm to room temp. Stir at room temp. overnight. TLC (95:5, CH$_2$Cl$_2$:MeOH) Rf (st mat.)=0.26. Rf(prod)=0.46 After 22 hours at room temp., the reaction was cooled to 0° C., and quenched with H$_2$O/EtOAc. Extracted aq. with EtOAc. Washed comb. org. with water(5x), brine, dried MgSO$_4$, filter, concentrated in vacuo. Purified by chrom., (40% ether/CH$_2$Cl$_2$) to yield 310 mg(37%).

| B. | | |
|---|---|---|
| 1 | lactam | 1.15 g, 1.0 equiv. |
| 2 | t-butyldimethylsilyl trifluoromethanesulfonate | 1.5 equiv. + .5 eq., (1.06 mL) |
| 3 | imidazole | 2.5 equiv + .5 eq, (470 mg) |
| 4 | DMF | |

Dissolve 1.15 g of 1 in 5 mL of DMF. Cool to 0° C. Add 390 mg of 3 as a solid. After stirring for 5 min. at 0° C., 795 UL of 2 was added. Stir at 0° C. for 5 min., then warm to room temp. After approximatly 2 hours an additional 0.5 eq.(80 mg) of 2 and 0.5 eq.(265 uL) of 3 was added and the reaction stirred overnight. The reaction was quenched with sat'd NaHCO$_3$ solution, partitioned between H$_2$O/EtOAc, extracted aq. with EtOAc. Washed comb. org. with water (4x), brine, dry MgSO$_4$, filtered, and concentrated in vacuo to give 1.5 g of silyl material used as is.

| C. | | |
|---|---|---|
| 1 | silyl-lactam | 1.0 equiv., 23 mg |
| 2 | Allyl Bromide, | 2.1 equiv., 7 uL |
| 3 | LDA, 1.29M | 1.25 equiv, 36 uL |
| 4 | TBAF, 1.0M, | 2.5 equiv., 95 uL: |

Dissolve 1 in THF. Cool to −78° C. Add 3 via syringe After stirring for 30 min. at −78° C., 5 uL of 2 was added via syringe. After ~2 hours an additional 2 ul of 2 was added. Stirred at −78° C. for 2.5 hours, then warmed to room temp for 17 hours. TLC (2:8, ether:CH$_2$Cl$_2$) Rf (st mat.)=0.56. Rf(silyl-prod)=0.72. Add 4, then stir ar room temp. until complete (7 hours) TLC (1:9, ether:CH$_2$Cl$_2$) Rf(prod)=0.20 Partition bet. H$_2$O/EtOAc. Extract aq. with EtOAc. Wash comb. organics with water, brine, dry MgSO$_4$, filter, concentrate in vacuo. Purified by chrom., 10% ether/CH$_2$Cl$_2$ to give 6 mg(30% yield)

| D. | | |
|---|---|---|
| 1 | silyl-lactam | 1.0 equiv., 122 mg |
| 2 | benzyl bromide, | 1.5 equiv. 42 uL |
| 3 | LDA, 1.29M | 1.4 equiv, 275 ul |
| 4 | TBAF, 1.0M, | 2.5 equiv., 625 uL |

Dissolve 122 mg of 1 in 6 mL THF. Cool to −78° C. Add 275 uL of 3 via syringe. After stirring for 30 min. at −78° C., 42 uL of 2 was added via syringe. Stirred at −78° C. until reaction was complete(1.5 hours). TLC (1:9, ether:CH$_2$Cl$_2$) Rf (st mat.)=0.29. Rf(silyl-prod)=0.62. Rf(BzBr)=0.79. Quench at −78° C. with 6 uL water. Add 625 uL of 4, then warm to room temp. Stir ar room temp. until complete ('3 hours) TLC (1:9, ether:CH$_2$Cl$_2$) Rf(prod)=0.28 Partition bet. H$_2$O/EtOAc. Extract aq. with EtOAc. Wash comb. organics with water, brine, dry MgSO$_4$, filter, concentrate in vacuo. Purified by chrom., 10% ether/CH$_2$Cl$_2$ to give 71 mg (48%) yield

| E. | | |
|---|---|---|
| 1 | silyl-lactam | 1.0 equiv., 66 mg |
| 2 | Methyl iodide, | 1.6 equiv., 16 uL |
| 3 | LDA, 1.29M | 1.3 equiv, 110 uL |
| 4 | TBAF, 1.0M, | 3.0 equiv., 325 uL: |

Dissolve 1 in THF. Cool to −78° C. Add 3 via syringe After stirring for 60 min. at −78° C., 2 was added via syringe. Stirred at −78° C. until reaction was complete(2 hours). TLC (2:8, ether:CH$_2$Cl$_2$) Rf (st mat.)=0.21. Rf(silyl-prod)=0.47. the reaction was quenched at −78° C. with 6 uL water. Add 4, then warm to room temp. Stir ar room temp. until complete (4 hours) TLC (1:9, ether:CH$_2$Cl$_2$) Rf(prod)=0.25 Partition bet. H$_2$O/EtOAc. Extract aq. with EtOAc. Wash comb. organics with water, brine, dry MgSO$_4$, filter, concentrate in vacuo. Purified by chrom., 10% ether/CH$_2$Cl$_2$ to give 33 mg(60% yield)

Example 4

| A. | | | |
|---|---|---|---|
| 1 | lactam from 2B | 1.0 equiv., 400 mg | |
| 2 | epibromohydrin | 1.5 equiv., 280 uL | |
| 3 | sodium hydride, 80% oil disp. | 2.0 equiv, 126 mg | |
| | DMF | 15 mL | |

Dissolve 1 in 15 mL of DMF. Cool to 0° C. under nitrogen. Add 2 in one portion. Stir at 0° C. for 1 hour then add 3 via syringe. After stirring for 5 min. at 0° C. the reaction was warmed to room temp. TLC (EtOAc) Rf (st mat.)=0.16. Rf(prod)=0.23. After 1.5 hours at room temp. the reaction was quenched with sat'd NH$_4$Cl and CH$_2$Cl$_2$. Extract aq. with CH$_2$Cl$_2$. Wash comb. org. with water(4x), brine, dry MgSO$_4$, filter, concentrate in vacuo. Purified by chromatagraphy (3:1 EtOAC:hexane) to yield 315 mg of ester(60%).

| B. | | |
|---|---|---|
| 1 | lactam from 4A | 1.0 equiv., 315 mg |
| 2 | cyclopentylamine | 5.75 equiv., 775 mg |
| | anhy. EtOH | 3 mL |

Dissolve 1 in 2 mL of EtOH. Add 2 with 1 mL of EtOH. Heat to 80° C. for 2.5 hours. TLC (9:1, CH$_2$Cl$_2$:MeOH) Rf (st mat.)=0.56. Rf(prod)=0.13. The solvent was removed in vacuo. Purified by chromatagraphy (3% MeOH/CH$_2$Cl$_2$ to 10% MeOH/CH$_2$Cl$_2$) to yield 224 mg(50%).

| C. | | |
|---|---|---|
| 1 | lactam | 1.0 equiv., 315 mg |
| 2 | chlorotrimethylsilane | 2.2 equiv., 112 uL |
| 3 | triethylamine | 5.0 equiv., 280 uL |
| 4 | 4-methoxybenzenesulfonyl chloride | 1.5 equiv., 124 mg |
| 5 | TBAF, 1.0M | 4.4 equiv., 1.78 mL |

Dissolve 1 in 15 mL of CH$_2$Cl$_2$. Cool to 0° C. Add 140 uL of 3 then add 112 uL of 2 and 2 mL of CH$_2$Cl$_2$. Warm to room temp. and stir under nitrogen for 2.0 hours. Add another 140 uL of 3 and 124 mg of 4 as a solid and stir at room temp for ~3 hours. 5 was added and the reaction stirred at room temp. for 1 hour. The solvent was removed in vacuo. and the residue partitioned between EtOAc/sat'd bicarb sol'n. Wash organics with water, brine, dry MgSO$_4$, filtered and the solvent removed in vacuo. TLC (8:2, CH$_2$Cl$_2$: ether), Rf(upper diast.)=0.21 Rf(lower diast.)=0.12. Purified by chromatagraphy (25% ether/CH$_2$Cl$_2$) to yield 52 mg(26%) of VB-18,481(upper diast.) The lower diastereomer was further purified by prep TLC(1:1, ether:CH$_2$Cl$_2$) to give 23 mg(12%) of compound 38.

Example 5

A.

Synthesis of 2-oxo-3-methyl-6-phenylmethylmorpholine. Dissolve S-(–)-2-Amino-3-phenyl-1-propanol (1.51 g, 10 mmol) in THF (10 ml).

To 0° C. solution add (rac)-2-bromopropionyl bromide (1.04 ml, 10 mmol), followed by a dropwise addition of diisopropylethylamine (1.73 ml, 10 mmol). Warm up to rt and continue stirring for 90 min. Remove solvents in vacuo and remove salts by ethyl acetate/water extraction (3x). Following magnesium sulfate drying, the ethyl acetate layer is evaporated and residue redissolved in anhydrous THF. To 0° C. solution add 13 mM of NaH (from 60% mineral oil dispersion, removed by washing, with hexane). Solution was warmed up to rt and reaction terminated (MeOH) after 1 hr. Residue left after solvents removal was again partitioned between ethyl acetate/water (2x), organic phases combined, dried with magnesium sulfate, filtered and evaporated, resulting in 1.20 g crude product. Silica gel chromatography (ethyl acetate) yielded 0.70 g of pure product, 34% yield. $^1$H NMR (CDC13): 7.25 (m, 5H), 6.75 (broad s, 1H), 4.19 (q, 1H, J=7.0 Hz), 3.76 (2H, d, J=7.5 Hz), 3.57 (1H, m), 2.90 (2H, m), 1.49+1.46 (both s, total integration 3H). CHN: 70.0 (calc: 70.2), 7.3 (7.4), 6.8 (6.8). Mass Spec. (API-)=204 (M-1). Silica gel plates: Rf=0.19 (1/1 ethyl acetate/hexane). HPLC at 220 nm (YMC 0.46 cmx25 cm C$_{18}$ reverse phase) t=11.47 min (single peak), gradient: 0–100% B/30 min, 1.5 ml/min, A=0.1% TFA in water, B=0.1% TFA in acetonitrile.

B.

Synthesis of 2-oxo-3,3-dimethyl6-phenylmethylmorpholine.

Dissolve 3.02 g (20 mM) of S-(–)-2-Amino-3-phenyl-1-propanol in 10 ml THF. To 0° C. solution add 2-Bromoisobutyryl bromide (2.47 ml, 20 mmol), followed by dropwise addition of diisopropylethylamine (3.47 ml, 20 mmol). Warm up to rt and continue stirring for 90 min. Remove solvents in vacuo and remove salts by ethyl acetate/water extraction (3x). Following magnesium sulfate drying, the ethyl acetate layer is evaporated and residue redissolved in anhydrous THF. Following silica gel chromatography (1/1 ethyl acetate/hexane), 1.20 g of intermediate 6 is isolated from mixture containing overacylation product.

To 0° C. solution of 6 in 4 ml of anhydrous DMF add 4 mM of NaH (from 60% mineral oil dispersion, removed by washing with hexane).

After 14 hrs at rt, the solvent was removed and solid residue partitioned between ethyl acetate/water (2x), organic phases combined, filtered, evaporated and (silica gel) chromatographed with ethyl acetate, resulting in 0.20 g of product homogenous by TLC, but heterogeneous by HPLC.

C.

Synthesis of 2-oxo-3,3-spirocyclohexyl6-phenylmethylmorpholine.

A solution containing, 1-bromocyclohexylcarboxylate (0.5 g, 2.4 mmol) and anhydrous DMF (3 ml) was diluted with S-(+)-2-amino-3-cyclohexyl-1-propanol hydrochloride (0.465 g, 2.4 mmol), N,N'-ethyl-dimethylaminopropylcarbodiimide hydrochloride (0.69 g, 3.6 mmol) and diisopropylethylamine (1.25 ml, 7.2 mmol). After stirring at room temperature for 2 hrs, the reaction was concentrated in vacuo. The crude product was purified by ethyl acetate/water extraction (3x), followed by drying with magnesium sulfate drying, resulting in 0.45 g (1.3 mM) of clear oil. The product was then redissolved in 3 ml anhydrous DMF, cooled to 0° C., added 67.7 mg (17 nmM) of NaH (from 60% mineral oil dispersion, removed by washing with hexane) and stirred for 30 hrs at 50° C. Reaction was then terminated and solvent removed, following by ethyl acetate/aqueous citric acid workup, resulting in 0.19 g (0.72 mM), yield 30%, of the desired product. 1H NMR consistent w/structure.

D.
   Synthesis of 47.
   Dissolve 0.16 g (0.60 mM) of the compound of Example 5C in 1 ml anhydrous DMF. Cool to 0° C. and add NaH (from 0.029 g, 0.73 mM, 60% mixture with mineral oil, removed with hexane). Bring to rt for 30 min, then cool down again to 0 ° C. and add 0.19 g of N,N-glyicidylcyclopentylmethyl-4-methoxyphenylsulfonamide (0.60 mM) in 1 ml anhydrous THF. Heat for 16 hrs at 50° C., then quench with acetic acid. Purified by silica gel chromatography. Mass spec (ESP+) 591.1 (M+1), 'HPLC1= 22.42 min, Rf=0.47 (1/1 ethyl acetate/hexane). 1H NMR consistent w/structure.
   HPLC1: at 220 nm (YMC 0.46 cm×25 cm $C_{18}$ reverse phase) t=11.47 min (single peak), gradient: 0–100% B/30 min, 1.5 ml/min, A=0.1% TFA in water, B=0.1% TFA in acetonitrile.

E.
   Synthesis of sulfonylurea
   50 g (167 mMol) of Cbz-(L)-Phenylalanine, 16.58 g(170 mMol) of N,O-dimethylhydroxlyamine hydrochloride, 25.16 g (170 mMol) of N-hydroxybenzotriazole, and 37.3 mL of N-methylmorpholine were dissolved in 500 mL of dimethylformamide and cooled on an icebath. 32.64 g (170 mMol) of EDCI were added and the resulting mixture was allowed to warm to rt. After stirring for 12 h, the volatiles were removed and the residue was partitioned between ethyl acetate and 1N HCl. Washing with satd. aqueous sodium bicarbonate, drying over magnesium sulfate and removal of the solvent in vacuo afforded 60 g of a yellow colored oil.

20 g of the crude product from the previous step were dissolved in 200 mL of THF, cooled to −78° and treated dropwise with 32 mL (32 mMol) of 1M lithium aluminum hydride in THF. The reaction mixture was allowed to warm to rt and was then poured into a mixture of ice and 6N HCl. Ethyl acetate was added, the layers were separated and the organic layer was washed with 10% aqueous sodium bicarbonate. Drying over magnesium sulfate and removal of the solvent in vacuo afforded the desired aldehyde (15.6 g) as a white solid.

7.0 g of the crude aldehyde from the previous step were dissolved in 40 mL of THF and added dropwise to a cooled (−78°) solution of 128 mL (128 mMol) of 1M trimethylsilyl methylmagnesium bromide in ether. The resulting mixture was allowed to warm to rt and poured into water. After diluting with ethyl acetate and 1N HCl, the layers were separated and the organic layer was washed with 10% aqueous sodium bicarbonate. Drying over magnesium sulfate and removal of the solvent in vacuo gave a viscous oil, which was re-dissolved in 150 mL of dichloromethane and treated dropwise with 15.6 mL of borontrifluoride etherate. The resulting mixture was stirred for 5 days at rt and then quenched with 10% NaOH. The organic layer was dried and evaporated and the residue was chromatographed on silica gel (20% ethyl acetate/hexanes) to give 5.2 g of a yellow solid.

Recrystallization from hexane yielded 4.6 g of the desired alkene as a white solid in three crops.

2.0 g (7.1 mMol) of the alkene from the previous step were mixed with 10 mL of carbon tetrachloride and 1.4 mL (20 mMol) of thioacetic acid. A spatula tip of AIBN was added and the mixture was irradiated in a quartz vessel at 254 nm for 2 h. The resulting mixture was diluted with dichloromethane and extracted with satd. aqueous sodium bicarbonate. Drying and removal of the solvent, followed by chromatography on silica gel (15% ethyl acetate/hexane) gave the desired thioacetate (2.0 g) as a pale yellow liquid which solidified on standing.

A solution of 0.85 g of the thioacetate from the previous step in 30 mL of acetic acid and 15 mL of 1N HCl was cooled on ice and exposed to a stream of chlorine gas for 2 h. Ethyl acetate was added and the organic layer was separated, dried and coevaporated with toluene to give the desired sulfonyl chloride as a white solid (1.05 g).

0.7 g of the sulfonyl chloride obtained in the previous step were dissolved in 30 mL of 30% HBr in acetic acid. After 2 h, the volatiles were removed in vacuo, the gummy residue was redissolved in 100 mL of chloroform and the solution was treated with 1 mL of triethylamine. The mixture was stirred for 1 h and then extracted with 1N HCl and 10% aqueous sodium bicarbonate. Drying over magnesium sulfate and removal of the solvent gave a brown oil which was chromatographed on silica gel (2% MeOH/dichloromethane) to give the desired sulfonamide as an off-white solid (0.305 g). 1H-NMR (CDC13): 2.20 (1H,m), 2.48 (1H,m), 2.89 (2H,m), 3.10 (1H,m), 3.23 1H,m), 3.84 (1H,m), 4.18 (1H, bs), 7.30 (5H,m). 13C-NMR (CDC13): 28.8, 42.0, 47.8, 56.2, 127.8, 129.1, 129.3, 136.6.

A solution of 30 g of Cbz-(L)-phenylalanine, 6.8 g of methylamine hydrochloride, 14.8 g of hydroxybenzotriazole and 22 mL of N-methylmorpholine in 300 mL of dimethylformamide was cooled on an ice-bath and treated with 19.2 g of EDCI. The mixture was allowed to reach rt overnight and then poured into 2000 mL of water. The product was collected by filtration, dried and redissolved in 500 mL of methanol and 300 mL of THF. 1 g of 5% palladium on carbon was added and the mixture was stirred under hydrogen for 36 h. Filtration and removal of the solvent, followed by short plug filtration through silica gel (5% MeOH(2M NH3)/dichloromethane) gave the desire amine as a pale yellow solid (17 g).

A solution of 1.22 g (56 mMol) of lithiumborohydride in 28 mL of THF was treated with 14.2 mL (112 mMol) of chlorotrimethyl silane. The resulting mixture was treated scoopwise with 5 g (28 mMol) of the amide from the previous step. After stirring at rt for 24 h, 40 mL of methanol were added carefully, followed by 10 mL of acetic acid. Repeated evaporation from methanol gave a colorless glass, which was dissolved in 100 mL of 20% NaOH. Extraction with 4×50 mL of chloroform, followed by drying and removal of the solvent gave a yellow oil which was chromatographed on silica gel (20% methanol(2M ammonia)/dichloromethane to give 1.5 g of the desired diamine as a colorless oil, and 2.0 g of recovered starting material.

0.15 g of the diamine from the previous step were dissolved in 0.5 mL of pyridine and added dropwise to a refluxing solution of 0.1 g of sulfonyldiimide in 1.5 mL of pyridine. Reflux was continued for 24 h and the volatiles were removed in vacuo. The resulting brown oil was chromatographed on silica gel (20% methanol(2M ammonia)/dichloromethane) to give the desired sulfonylurea as a yellow oil (0.04 g). $^1$H-NMR (CD$_3$OD): 2.60 (3H,s), 2.86 (1H,dd), 2.96 (1H,dd), 3.15 (1H,dd), 3.47 (1H,dd), 4.18 (1H,m), 7.22 (5H,m), 7.38 (1H,d). $^{13}$C-NMR (CD$_3$OD): 31.8, 39.9, 50.0, 57.8, 126.5, 128.2, 129.0, 136.6

Example 6

Using the method described by Pennington et al. (supra), we obtained inhibition constants for the following compounds of this invention:

| Compound | $K_i$ (nM) |
|---|---|
| 2* | 180 |
| 3* | 1,800 |
| 8* | 5 |
| 9* | 90 |
| 13 | 225 |
| 14 | 16 |
| 15 | 550 |
| 16 | 56 |
| 17 | 115 |
| 18 | 15 |
| 19 | 3,000 |
| 20 | 1.5 |
| 21 | >20,000 |
| 22 | 600 |
| 23 | 70 |
| 24 | 350 |
| 25 | 83 |
| 26 | 58 |
| 27 | 3,000 |
| 28 | 1,400 |
| 30 | >15,000 |
| 31 | 390 |
| 32 | 160 |
| 33 | 1,100 |
| 34 | 950 |
| 35 | 130 |
| 36 | >20,000 |
| 37 | >20,000 |
| 38 | 17 |
| 39 | 600 |
| 40 | >20,000 |
| 41 | >20,000 |
| 45 | 30 |

*Inhibition constant measured at pH 6.0.

The above data show that each of the tested compounds inhibits HIV aspartyl protease.

While we have described a number of embodiments of this invention, it is apparent that our basic constructions may be altered to provide other embodiments which utilize the products and processes of this invention. Therefore, it will be appreciated that the scope of this invention is to be defined by the appended claims, rather than by the specific embodiments which have been presented by way of example.

We claim:

1. A compound according to formula I:

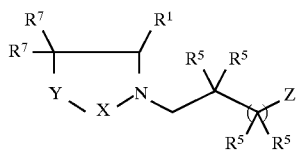

wherein:

each Z is

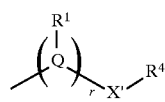

wherein Z is unfused or fused with $R^6$;

each X and X' is independently selected from the group consisting of —C(O)—, —C(O)C(O)—, —S(O)— and —S(O)$_2$;

each Y and Y' is independently selected from the group consisting of —(C($R^2$)$_2$)$_p$—, —$NR^2$—, —(C($R^2$)$_2$)$_p$M—, and —N($R^2$)—CH$_2$—;

each $R^1$ is independently selected from the group consisting of hydrogen; $R^6$; $C_1$–$C_6$ alkyl; $C_2$–$C_6$ alkenyl; $C_2$–$C_6$ alkynyl; $C_3$–$C_6$ cycloalkyl unfused or fused with $R^6$; $C_5$–$C_6$ cycloalkenyl unfused or fused with $R^6$; and where $R^1$'s are attached to adjacent atoms, the $R^1$'s together with their attached adjacent atoms form a carbocyclic or heterocyclic ring system which is unfused or fused with $R^6$; where any member of $R^1$ is unsubstituted or substituted by one or more $R^2$;

each $R^2$ is independently selected from hydrogen; $R^3$; $C_1$–$C_6$ alkyl; $C_2$–$C_6$ alkenyl; $C_2$–$C_6$ alkynyl; $C_3$–$C_6$ cycloalkyl unfused or fused with $R^6$; $C_5$–$C_6$ cycloalkenyl unfused or fused with $R^6$; and where two $R^2$'s are attached to the same geminal atom, the $R^2$'s together with their attached geminal atom form a spirocarbocyclic or spiroheterocyclic ring system, where any member of $R^2$ is unsubstituted or substituted by one or more $R^3$;

each $R^3$ is independently selected from oxo, $OR^9$, $N(R^9)_2$, $N(R^9)$—X—$R^9$, $N(R^9)$—X—$OR^9$, $SR^9$, X—$R^9$, O—X—$N(R^9)_2$, $C(O)N(R^9)_2$, halogen, $NO_2$, CN, $COOR^9$ and $R^6$;

each $R^4$ is independently selected from the group consisting of $OR^9$; $N(R^9)_2$; X—$R^9$; $C(O)N(R^9)_2$; $R^6$; $C_1$–$C_6$ alkyl; $C_2$–$C_4$ alkenyl; $C_3$–$C_6$ cycloalkyl unfused or fused with $R^6$; $C_5$–$C_6$ cycloalkenyl unfused or fused with $R^6$; where any member of $R^4$ is unsubstituted or substituted by one or more groups independently selected from the group consisting of $R^9$ and $R^3$;

each $R^5$ is independently selected from the group consisting of H, OH, O and $R^1$;

each $R^6$ is independently selected from the group consisting of aryl, carbocyclyl and heterocyclyl, wherein said aryl, carbocyclyl or heterocyclyl is unsubstituted or substituted with one or more groups selected from the group consisting of oxo, —$OR^9$, —$R^9$, —$N(R^9)(R^9)$, —$N(R^9)$—X—$R^9$, $SR^9$, —X—$R^9$, —O—X—N($R^9$)$_2$, —$R^9$—$OR^9$, —CN, —$CO_2R^9$, —X—N($R^9$)($R^9$), halogen, —$NO_2$, and —$CF_3$;

each $R^7$ is independently selected from the group consisting of hydrogen, OH and O;

each $R^8$ is independently selected from the group consisting of hydrogen, alkyl, alkenyl, alkynyl, aryl, carbocyclyl, and heterocyclyl;

each $R^9$ is independently selected from the group consisting of hydrogen, alkyl, alkenyl, alkynyl, aryl, carbocyclyl, heterocyclyl, aralkyl, carbocyclylalkyl and heterocyclylalkyl wherein any aryl, carbocyclyl or heterocyclyl is unfused or fused with $R^8$ and wherein any member of $R^8$ is unsubstituted or substituted by one or more groups independently selected from the group consisting of —$OR^8$, —$N(R^8)_2$, —CN, —$NO_2$, —X—$R^8$, —X—$N(R^8)_2$, —$C(O)OR^8$, —$N(R^8)$—XN$R^8$, and halogen;

each Q is independently selected from CH and N;

each M is independently selected from the group consisting of NH, —$NR^2$—, —O—, —S—, —S(O)— and —S(O)$_2$—;

each n is 1 or 2;

each r is 0, 1 or 2; and each p is independently 1 or 2.

2. The compound according to claim 1, wherein n is equal to 1.

3. The compound according to claim 1 having the structure of formula II:

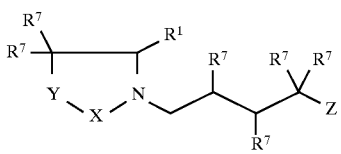

4. The compound according to claim 1 having the structure of formula III:

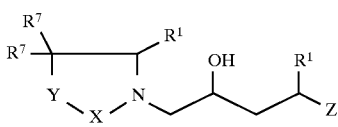

5. The compound according to claim 1, wherein
X is —C(O)— or —S(O)$_2$—; and
Y is —(C(R$^2$)$_2$)$_p$—M—.

6. The compound according to claim 1, wherein
X is —C(O)— or —S(O)$_2$—; and
Y is (—C(R$^2$)$_2$—)$_p$.

7. The compound according to claim 1, wherein
X is —C(O)—, —C(O)C(O)— or —S(O)$_2$—; and
Y is —N(R$^2$)— or —N(R$^2$)—CH$_2$—.

8. The compound according to claim 1, having the structure of formula IV:

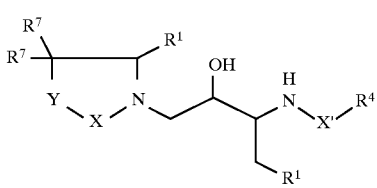

wherein
X and X' are independently —C(O)— or —S(O)$_2$—; and
Y is —(C(R$^2$)$_2$)—M—, —(C(R$^2$)$_2$)$_p$—, —N(R$^2$)— or —N(R$^2$)—CH$_2$—.

9. The compound according to claim 1, having the structure of formula IX:

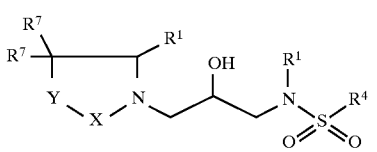

wherein
X is —C(O)— or —S(O)$_2$—.

10. The compound according to claim 9, wherein
X is —C(O)—;
Y is —(C(R$^2$)$_2$)—M—; and
R$^7$ is H.

11. The compound according to claim 9, wherein
X is —C(O)—;
Y is —N(R$^2$)—; and
R$^7$ is H.

12. The compound according to claim 9, wherein
X is —C(O)—;
Y is —(C(R$^2$)$_2$)—; and
R$^7$ is H.

13. The compound according to claim 1, having the structure of formula XII:

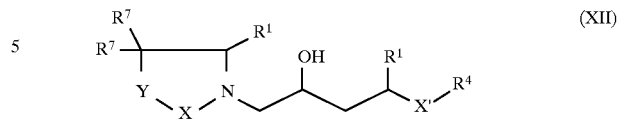

wherein

X and X' are independently —C(O)— or —S(O)$_2$—.

14. The compound according to claim 1, having the structure of formula XIII:

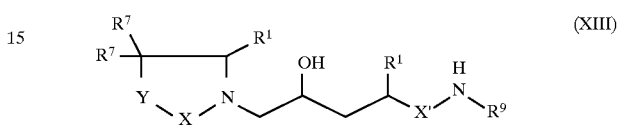

wherein

X and X' are independently —C(O)— or —S(O)$_2$—.

15. The compound according to claim 1, wherein

Z is selected from the group consisting of —XR$^4$, —N(R$^1$)—X—R$^4$, —N(R$^1$)—N(R$^1$)—X—R$^4$, and formula VI; wherein any structure of formula VI is unfused or fused with an aryl, carbocyclic or heterocyclic ring and is unsubstituted or substituted with 1–3 members independently selected from R$^2$.

16. A pharmaceutical composition comprising a pharmaceutically effective amount of a compound according to claim 1 and a pharmaceutically acceptable carrier, adjuvant or vehicle.

17. The pharmaceutical composition according to claim 16, wherein said pharmaceutical composition is orally administrable.

18. A method for inhibiting aspartyl proteas activity comprising the step of contacting an aspartyl protease with the compound according to claim 1.

19. A method for reversibly binding an aspartyl protease comprising the step of contacting the aspartyl protease with the compound according to claim 1, said compound being covalently bound to a solid matrix.

20. A method for treating HIV infection in a mammal comprising the step of administering to said mammal a pharmaceutically effective amount of a pharmaceutical composition according to either claim 14.

21. A method for treating HIV infection in a mammal comprising the step of administering to said mammal a pharmaceutically effective amount of a pharmaceutical composition according to claim 16.

22. A method for treating a viral infection in a mammal comprising the step of administering to said mammal a pharmaceutically effective amount of a pharmaceutical composition according to either claim 1.

23. The composition according to claim 16, wherein the additional anti-viral agents are 3TC and zidovudine (AZT).

24. The compound of claim 1, selected from the group consisting of:

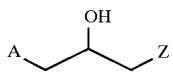

wherein A and Z are as shown below:

| Cmpd. No. | A | Z |
|---|---|---|
| 1 | 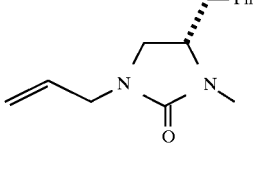 | 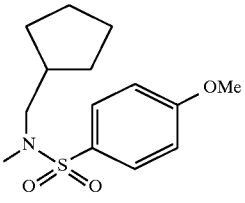 |
| 4 | 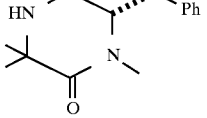 | 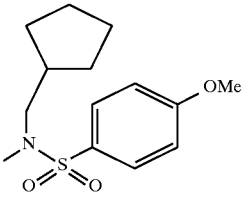 |
| 7 | 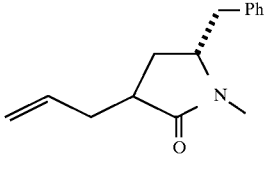 | 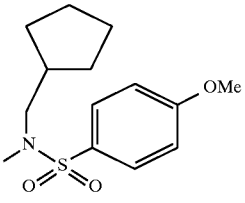 |
| 13 | 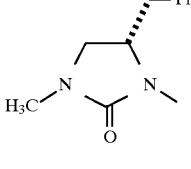 | 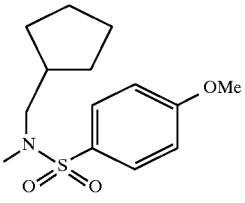 |
| 14 | 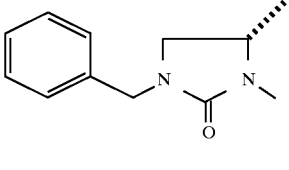 | 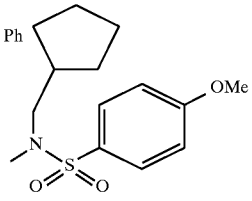 |
| 16 | 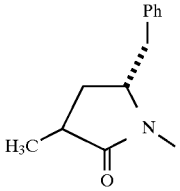 | 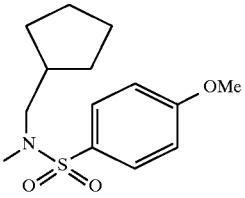 |
| 17 | 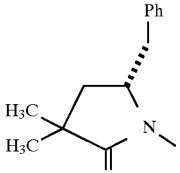 | 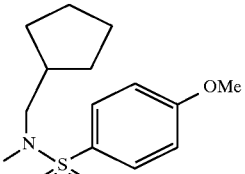 |

-continued

| Cmpd. No. | A | Z |
|---|---|---|
| 18 | | |
| 20 | | |
| 23 | | |
| 24 | | |
| 25 | | |
| 26 | | |
| 32 | | |

-continued

| Cmpd. No. | A | Z |
|---|---|---|
| 35 | | |
| 38 | | |
| 44 | | |
| 45 | | |
| 46 | | |
| 47 | | |
| 48 | | | wherein A, R[1] and Z are as shown below:

| Cmpd. No. | A | R[1] | Z |
|---|---|---|---|
| 59 | (1-benzyl-4-benzyl-3-methyl-imidazolidin-2-one) | Bn | (N-acetyl-2-hydroxyindanyl) |
| 60 | (5-benzyl-3-benzyl-1-methyl-pyrrolidin-2-one) | Bn | (N-acetyl-2-hydroxyindanyl) |

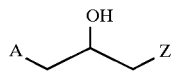

wherein A, R[1] and Z are as shown below:

| Cmpd No. | A | R[1] | Z |
|---|---|---|---|
| 81 | (5-benzyl-3-benzyl-1-methyl-pyrrolidin-2-one) | Bn | (N-methylcarbamate of tetrahydrofuranyl) |
| 82 | (3-benzyl-5-benzyl-2-methyl-isothiazolidine 1,1-dioxide) | Bn | (N-methylcarbamate of tetrahydrofuranyl) | wherein Bn is benzyl.

25. The compound of claim 24, selected from the group consisting of compound numbers:

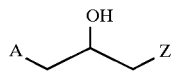

wherein A and Z are as shown below:

| Cmpd. No. | A | Z |
|---|---|---|
| 7 | (structure: N-methyl lactam with benzyl and allyl substituents) | (structure: cyclopentylmethyl-N(Me)-SO2-C6H4-OMe) |
| 14 | (structure: imidazolidinone with N-benzyl, N-methyl, and benzyl substituents) | (structure: cyclopentylmethyl-N(Me)-SO2-C6H4-OMe) |
| 18 | (structure: N-methyl lactam with benzyl and ethyl substituents) | (structure: cyclopentylmethyl-N(Me)-SO2-C6H4-OMe) |
| 20 | (structure: N-methyl lactam with benzyl and benzyl substituents) | (structure: cyclopentylmethyl-N(Me)-SO2-C6H4-OMe) |
| 25 | (structure: N-methyl lactam with benzyl and AcO-CH2-CH(OAc)-CH2 substituents) | (structure: cyclopentylmethyl-N(Me)-SO2-C6H4-OMe) |
| 26 | (structure: N-methyl lactam with benzyl and cyclic carbonate-substituted chain) | (structure: cyclopentylmethyl-N(Me)-SO2-C6H4-OMe) |
| 32 | (structure: 1-(N-methylcarbamoyl)cyclopentane with benzyl and HN-CH2 substituents) | (structure: cyclopentylmethyl-N(Me)-SO2-C6H4-OMe) |

26. The compound of claim 25, selected from the group consisting of compound numbers:
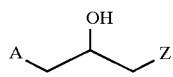
wherein A and Z are as shown below:

-continued
| Cmpd. No. | A | Z |
|---|---|---|
| 45 | 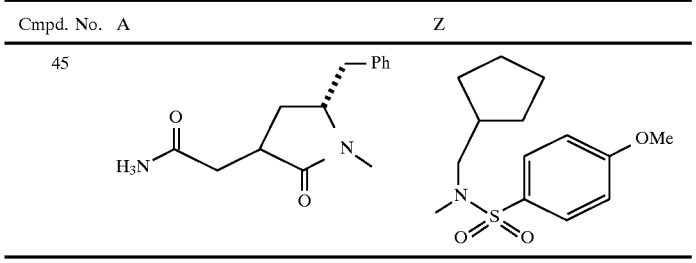 | |
* * * * *